United States Patent
Lan et al.

(10) Patent No.: US 9,434,714 B2
(45) Date of Patent: Sep. 6, 2016

(54) PYRIMIDINE IMIDAZOLE AMINES AS MODULATORS OF KINASE ACTIVITY

(71) Applicant: Merck Patent GmbH, Darmstadt (DE)

(72) Inventors: Ruoxi Lan, Waltham, MA (US); Xiaoling Chen, Chestnut Hill, MA (US); Yufang Xiao, Lexington, MA (US); Bayard R. Huck, Sudbury, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/618,122

(22) Filed: Feb. 10, 2015

(65) Prior Publication Data

US 2015/0225371 A1    Aug. 13, 2015

Related U.S. Application Data

(60) Provisional application No. 61/938,343, filed on Feb. 11, 2014.

(51) Int. Cl.
*A61K 31/506* (2006.01)
*C07D 401/14* (2006.01)

(52) U.S. Cl.
CPC ........... *C07D 401/14* (2013.01); *A61K 31/506* (2013.01)

(58) Field of Classification Search
CPC ........................... C07D 401/14; A61K 31/506
See application file for complete search history.

(56) References Cited

U.S. PATENT DOCUMENTS

| | | | | |
|---|---|---|---|---|
| 9,145,392 B2 * | 9/2015 | Lan | ...................... | C07D 401/14 |
| 2013/0079326 A1 * | 3/2013 | Tsui | ..................... | C07D 401/12 |
| | | | | 514/210.18 |

FOREIGN PATENT DOCUMENTS

| WO | WO 2010033977 A2 * | 3/2010 | ........... C07D 401/04 |
|---|---|---|---|
| WO | 2013040059 A1 | 3/2013 | |
| WO | WO 2013040059 A1 * | 3/2013 | ........... C07D 401/14 |

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*

B Testa et al., Prodrug Design in, 5 Encyclopedia of Pharmaceutical Technology, 3008-3014 (J. Swarbrick ed., 3rd ed., 2007).*
Barlund et al., Multiple Genes at 17q23 Undergo Amplification and Overexpression in Breast Cancer, Cancer Research, 2000, 60: 5340-5344.
Berge et al., Pharmaceutical Salts, J. Pharma Sciences, 1977, 66: 1-19.
Couch et al., Localization of PS6K to Chromosomal Region 17q23 and Determination of its Amplification in Breast Cancer, Cancer Research, 1999, 59: 1408-1411.
Foster, Allan B., •Deuterium Isotope Effects in the Metabolism of Drugs and Xenobiotics: Implications for Drug Design, Advances in Drug Research, 1985, 14: 1-39.
Garcia-Bustos et al., PIK1, an essential phosphatidylinositol 4-kinase associated with the yeast nucleus, The Embo Journal, 1994, vol. 13, 10: 2352-2361.
Gillette et al., Theory for the observed Isotope Effects on the Formation of Multiple Products by Different Kinetic Mechanisms of Cytochrome P450 Enzymes, Biochemistry, 1994, 33: 2927-2937.
Hanzlik et al., Active Site Dynamics of Toluene Hydroxylation by Cytochrome P-450, J. Org. Chem., 1990, 55: 3992-3997.
Hardie/Hanks, The Protein Kinase Facts Book. I and II, Academic Press, San Diego, CA, 1995.
Hiles et al., Phosphatidylinositol 3-Kinase: Structure and Expression of the 110 kd Catalytic Subunit, Cell, 1992, 70:419-429.
Jarman et al., The deuterium isotope effect for the a-hydroxylation of tamoxifen by rat liver microsomes accounts for the reduced genotoxicity of [D5-ethyl]tamoxifen, Carcinogenesis, 1995, vol. 16, 4:683-688.
Knighton et al., Crystal Structure of the Catalytic Subunit of Cyclic Adenosine Monophosphate-Dependent Protein Kinase, Science, 1991, 253:407-414.
Kunz et al., Target of Rapamycin in Yeast, TOR2, is an Essential Phosphatidylinositol Kinase Homolog Required for G Progression, Cell, 1993, 73:585-596.
The Periodic Table of the Elements, CAS version, Handbook of Chemistry and Physics, 75th Ed.
Organic Chemistry, Thomas Sorrell, University Science Books, Sausalito,1999.
March's Advanced Organic Chemistry, 5th Ed., Ed.: Smith, M.B. and March, J., John Wiley & Sons, New York: 2001.
Reider et al., Synthesis of (R)-Serine-2-d and its Conversion to the Broad Spectrum Antibiotic Fludalanine, J. Org. Chem. 1987, 52:3326-3334.
Wu et al., 17q23 Amplifications in Breast Cancer Involve the PAT1, RAD51C, PS6K, and SIGMA1B Genes, Cancer Research, 2000, 60:5371-5375.

* cited by examiner

*Primary Examiner* — Alexander R Pagano
(74) *Attorney, Agent, or Firm* — Dwight D. Kim; EMD Serono Research and Development Institute

(57) ABSTRACT

The invention provides novel imidazole amine compounds according to formula (I) their manufacture and use for the treatment of hyperproliferative diseases, such as cancer.

5 Claims, No Drawings

PYRIMIDINE IMIDAZOLE AMINES AS MODULATORS OF KINASE ACTIVITY

RELATED APPLICATIONS

This application claims the benefit of U.S. Provisional application 61/938,343, filed on Feb. 11, 2014, the contents of which are incorporated its entirety by reference.

FIELD OF THE INVENTION

The invention relates to a series of pyrimidine imidazole amine compounds that are useful in the treatment of hyperproliferative diseases, such as cancer, in mammals. Also encompassed by the present invention is the use of such compounds in the treatment of hyperproliferative diseases in mammals, especially humans, and pharmaceutical compositions containing such compounds.

BACKGROUND

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)). Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Protein kinase 70S6K, the 70 kDa ribosomal protein kinase p70S6K (also known as S6K, p70/p85 S6 kinase, p70/p85 ribosomal S6 kinase and p70S6K), is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. p70S6K activity is also under the control of a mTOR-containing complex (TORC1) since rapamycin acts to inhibit p70S6K activity. p70S6K is regulated by PI3K downstream targets AKT and PKCζ. Akt directly phosphorylates and inactivates TSC2, thereby activating mTOR. In addition, studies with mutant alleles of p70S6K that inhibited by Wortmannin but not by rapamycin suggest that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore, inhibition of cell cycle proliferation at the G1 to S phase of the cell cycle by rapamycin has been identified as a consequence of inhibition of the production of the hyperphosphorylated, activated form of p70S6K.

A role for p70S6K in tumor cell proliferation and protection of cells from apoptosis is supported based on it participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11-Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M. Barlund, O. Monni, J. Kononen, R. Cornelison, J. Torhorst, G. Sauter, O. -P. Kallioniemi and Kallioniemi A., Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed. Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported. In response to energy stress, the tumor suppressor LKB1 activates AMPK which phosphorylates the TSC1/2 complex and enables it to inactivate the mTOR/p70S6K pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations. p70S6K has been implicated in metabolic diseases and disorders. It was reported that the absence of p70S6K protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

SUMMARY OF THE INVENTION

It is an object of the present invention to provide novel compounds of formula (I) that modulate kinase activity:

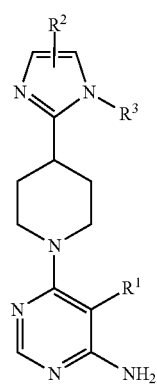

(I)

wherein $R^1$, $R^2$, and $R^3$ are as defined herein.

This protein kinase modulation includes, but is not limited to, p70S6K inhibition and Akt inhibition useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

DESCRIPTION OF THE INVENTION

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., ta Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

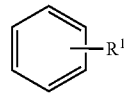

refers to at least

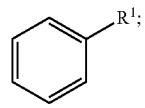

and

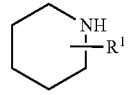

refers to at least

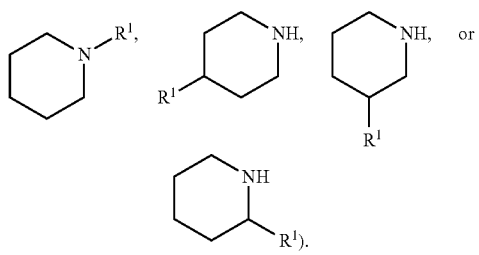

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH═CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°S(O)$_2$NR°$_2$; —N(R°S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —ON, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —ON, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)-heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$-alkyl, —OCO$_2$-alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl,
—NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkynyl, —NHC(O)NH— carbocyclyl, —NHC(O)NH-aryl, —NHC(O)NH-heteroaryl, —NHC(O)NH-heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— -alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl,
—C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl,
—S(O)— alkyl, —S(O)— alkenyl, —S(O)— alkynyl, —S(O)— carbocyclyl, —S(O)-aryl, —S(O)-heteroaryl, —S(O)-heterocyclyl-SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl,
—NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,
—CH$_2$NH$_2$, —CH$_2$SO$_2$CH$_3$,
-mono-, di-, or tri-alkyl silyl,
-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S— alkenyl, —S— alkynyl, —S— carbocyclyl, —S— aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C— or $^{14}$C-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability.

Incorporation of heavier isotopes, for example deuterium ($^2$H), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2$-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an 1050 and/or binding constant of less about 50 µM, less than about 1 µM, less than about 500 nM, less than about 100 nM, or less than about 10 nM.

The terms "measurable affinity" and "measurably inhibit," as used herein, mean a measurable change in p70S6K activity between a sample comprising a compound of the present invention, or composition thereof, and p70S6K, and an equivalent sample comprising p70S6K, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Compounds

It is the object of the present invention to provide novel compounds that modulate kinase activity. This protein kinase modulation includes, but is not limited to, p70S6K inhibition and Akt inhibition useful in the treatment of hyperproliferative diseases, especially those related to the hyperactivity of the above mentioned protein kinases, such as cancer in mammals, with superior pharmacological properties both with respect to their activities as well as their solubility, metabolic clearance and bioavailability characteristics.

In certain aspects, the invention provides compounds of formula (I):

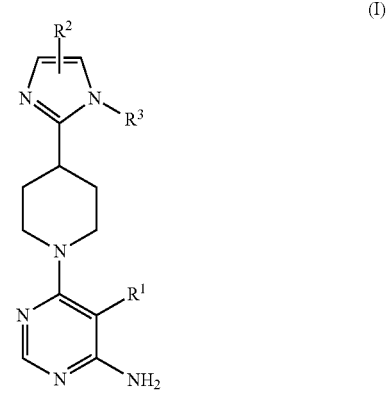

and pharmaceutically acceptable salts, solvates, solvates of salts, or prodrugs thereof, wherein:

$R^1$ is Hal, LA, OH, O(LA), $NH_2$ and/or NH(LA), $N(LA)_2$, $NO_2$, CN, OCN, SCN, COOH, COO(LA), $CONH_2$, CONH(LA), $CON(LA)_2$, NHCO(LA), NHCONH (LA), $NHCONH_2$, $NHSO_2$(LA), CHO, CO(LA), $SO_2NH_2$, $SO_2$(LA), or a $C_{5-10}$ aryl or $C_{6-15}$ fused aryl, a 3-12 membered saturated or partially unsaturated monocyclic or bicyclic carbocyclic ring, a 3-12 membered monocyclic or bicyclic heterocylic ring having 1-4 heteroatoms independently selected from nitrogen, oxygen, or sulfur, or a 5-12 membered monocyclic or bicyclic heteroaryl ring having 1-4 heteroatoms independently selected from nitrogen, oxygen, or sulfur; each of which is optionally mono-, di- or trisubstituted by Hal, LA, OH, O(LA), $NH_2$ and/or NH(LA), $N(LA)_2$, $NO_2$, CN, OCN, SCN, COOH, COO(LA), $CONH_2$, CONH(LA), $CON(LA)_2$, NHCO(LA), NHCONH (LA), $NHCONH_2$, $NHSO_2$(LA), CHO, CO(LA), $SO_2NH_2$, $SO_2$(LA) and/or $SO_2$H, or an unbranched or branched linear or cyclic alkyl having 1, 2, 3, 4, 5, 6, 7 or 8 C atoms, in which one or two $CH_2$ groups may be replaced by an O atom and/or by an —NH—, NH(LA), —CO—, —NHCO— or —CH=CH— group, and/or in which a CH group may be replaced by —N—;

$R^3$ is H, an unbranched or branched linear or mono- or bicyclic alkyl group having 1, 2, 3, 4, 5, 6, 7, 8 or 9 C atoms, in which one or two $CH_2$ groups may be replaced by an —O—, —NH—, group, and/or in which one or two CH groups may be replaced by —N—, and/or in which 1, 2 or 3 H atoms may be replaced by Hal or OH, $R^2$ is $C_{5-10}$ aryl or $C_{6-15}$ fused aryl, a 3-12 membered saturated or partially unsaturated monocyclic or bicyclic carbocyclic ring, a 3-12 membered monocyclic or bicyclic heterocylic ring having 1-4 heteroatoms independently selected from nitrogen, oxygen, or sulfur, or a 5-12 membered monocyclic or bicyclic heteroaryl ring having 1-4 heteroatoms independently selected from nitrogen, oxygen, or sulfur; each of which is optionally mono-, di- or trisubstituted by Hal, LA, OH, O(LA), $NH_2$ and/or NH(LA), $N(LA)_2$, $NO_2$, CN, OCN, SCN, COOH, COO(LA), $CONH_2$, CONH(LA), $CON(LA)_2$, NHCO(LA), NHCONH(LA), $NHCONH_2$, $NHSO_2$(LA), CHO, CO(LA), $SO_2NH_2$, $SO_2$(LA);

Hal is F, Cl, Br or I, and

LA is an unbranched or branched, saturated or partially unsaturated, linear hydrocarbon chain having 1, 2, 3 or 4 C atoms, wherein 1, 2 or 3 H atoms may be replaced by Hal.

In certain embodiments, the invention provides a compound of formula (I) wherein the following compounds, disclosed in WO 2013/040059 (PCT/US2012/054900), are excluded:

5-Bromo-6-{4-[4-(4-fluoro-3-trifluoromethyl-phenyl)-1-methyl-1H-imidazol-2-yl]-piperidin-1-yl}-pyrimidin-4-ylamine;

5-Bromo-6-{4-[5-(4-fluoro-3-trifluoromethyl-phenyl)-1-methyl-1H-imidazol-2-yl]-piperidin-1-yl}-pyrimidin-4-ylamine;

5-Bromo-6-{4-[4-(3-trifluoromethyl-phenyl)-1H-imidazol-2-yl]-piperidin-1-yl}-pyrimidin-4-ylamine;

5-Bromo-4-{4-[4-(3-trifluoromethyl-phenyl)-1H-imidazol-2-yl]-piperidin-1-yl}-pyrimidine;

3-bromo-4-(4-{4-[3-(trifluoromethyl)phenyl]-1H-imidazol-2-yl}piperidin-1-yl)pyridine;

4-Amino-6-{4-[4-(4-fluoro-3-trifluoromethyl-phenyl)-1-methyl-1H-imidazol-2-yl]-piperidin-1-yl}-pyrimidine-5-carbaldehyde;

4-Amino-6-{4-[4-(4-fluoro-3-trifluoromethyl-phenyl)-1-methyl-1H-imidazol-2-yl]-piperidin-1-yl}-pyrimidine-5-carbonitrile;

4-Amino-6-{4-[1-(2-dimethylamino-ethyl)-4-(4-fluoro-3-trifluoromethyl-phenyl)-1H -imidazol-2-yl]-piperidin-1-yl}-pyrimidine-5-carbonitrile;

6-{4-[4-(4-Fluoro-3-trifluoromethyl-phenyl)-1-methyl-1H-imidazol-2-yl]-piperidin-1-yl}-5-methoxy-pyrimidin-4-ylamine;

5-(4-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine;

6-{4-[4-(4-Fluoro-3-trifluoromethyl-phenyl)-1-methyl-1H-imidazol-2-yl]-piperidin-1-yl}-5-(4-methoxy-phenyl)-pyrimidin-4-ylamine;

6-{4-[4-(4-Fluoro-3-trifluoromethyl-phenyl)-1-methyl-1H-imidazol-2-yl]-piperidin-1-yl}-pyrimidin-4-ylamine;

6-{4-[4-(4-Fluoro-3-trifluoromethyl-phenyl)-1-methyl-1H-imidazol-2-yl]-piperidin-1-yl}-5-p -tolyl-pyrimidin-4-ylamine;

[4-(4-Amino-6-{4-[4-(4-fluoro-3-trifluoromethyl-phenyl)-1-methyl-1H-imidazol-2-yl]-piperidin-1-yl}-pyrimidin-5-yl)-phenyl]-methanol;

3-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile;

6-{4-[4-(4-Fluoro-3-trifluoromethyl-phenyl)-1-methyl-1H-imidazol-2-yl]-piperidin-1-yl}-5-(4-trifluoromethyl-phenyl)-pyrimidin-4-ylamine;

4-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile;

2-(4-Amino-6-{4-[4-(4-fluoro-3-trifluoromethyl-phenyl)-1-methyl-1H-imidazol-2-yl]-piperidin-1-yl}-pyrimidin-5-yl)-benzonitrile;

6-{4-[4-(4-Fluoro-3-trifluoromethyl-phenyl)-1-methyl-1H-imidazol-2-yl]-piperidin-1-yl}-5-(6-methyl-pyridin-3-yl)-pyrimidin-4-ylamine;

6-{4-[4-(4-Fluoro-3-trifluoromethyl-phenyl)-1-methyl-1H-imidazol-2-yl]-piperidin-1-yl}-5-(5-methyl-thiophen-2-yl)-pyrimidin-4-ylamine;

6-{4-[4-(4-Fluoro-3-trifluoromethyl-phenyl)-1-methyl-1H-imidazol-2-yl]-piperidin-1-yl}-5-phenyl-pyrimidin-4-ylamine;

5-(3-Fluoro-phenyl)-6-{4-[4-(4-fluoro-3-trifluoromethyl-phenyl)-1-methyl-1H-imidazol-2-yl]-piperidin-1-yl}-pyrimidin-4-ylamine;

5-(2-Fluorophenyl)-6-{4-[4-(4-fluoro-3-trifluoromethyl-phenyl)-1-methyl-1H-imidazol-2-yl]-piperidin-1-yl}-pyrimidin-4-ylamine;

5-(2-Chlorophenyl)-6-{4-[4-(4-fluoro-3-trifluoromethyl-phenyl)-1-methyl-1H-imidazol-2-yl]-piperidin-1-yl}-pyrimidin-4-ylamine;

6-{4-[4-(4-Fluoro-3-trifluoromethyl-phenyl)-1-methyl-1H-imidazol-2-yl]-piperidin-1-yl}-5-(6-morpholin-4-yl-pyridin-3-yl)-pyrimidin-4-ylamine;

6-{4-[4-(4-Fluoro-3-trifluoromethyl-phenyl)-1-methyl-1H-imidazol-2-yl]-piperidin-1-yl}-5-(6-piperazin-1-yl-pyridin-3-yl)-pyrimidin-4-ylamine;

5-(6-Fluoro-pyridin-3-yl)-6-{4-[4-(4-fluoro-3-trifluoromethyl-phenyl)-1-methyl-1H-imidazol-2-yl]-piperidin-1-yl}-pyrimidin-4-ylamine;

6'-{4-[4-(4-Fluoro-3-trifluoromethyl-phenyl)-1-methyl-1H-imidazol-2-yl]-piperidin-1-yl}-[5,5']bipyrimidinyl-2,4'-diamine;

6-{4-[4-(4-Fluoro-3-trifluoromethyl-phenyl)-1-methyl-1H-imidazol-2-yl]-piperidin-1-yl}-5-(3-methoxyphenyl)-pyrimidin-4-ylamine;

5-(3,4-Difluoro-phenyl)-6-{4-[4-(4-fluoro-3-trifluoromethyl-phenyl)-1-methyl-1H-imidazol-2-yl]-piperidin-1-yl}-pyrimidin-4-ylamine;

6'-{4-[4-(4-Fluoro-3-trifluoromethyl-phenyl)-1-methyl-1H-imidazol-2-yl]-piperidin-1-yl}-N2,N2-dimethyl-[5,5']bipyrimidinyl-2,4'-diamine;

5-(4-Aminomethyl-phenyl)-6-{4-[4-(4-fluoro-3-trifluoromethyl-phenyl)-1-methyl-1H -imidazol-2-yl]-piperidin-1-yl}-pyrimidin-4-ylamine;

5-(4-Methoxy-phenyl)-6-{4-[4-(3-trifluoromethyl-phenyl)-1H-imidazol-2-yl]-piperidin-1-yl}-pyrimidin-4-ylamine;

5-(4-Methoxy-phenyl)-4-{4-[4-(3-trifluoromethyl-phenyl)-1H-imidazol-2-yl]-piperidin-1-yl}-pyrimidine;

3-(4-methoxyphenyl)-4-(4-{4-[3-(trifluoromethyl)phenyl]-1H-imidazol-2-yl}piperidin-1-yl)pyridine;

(4-Amino-6-{4-[4-(4-fluoro-3-trifluoromethyl-phenyl)-1-methyl-1H-imidazol-2-yl]-piperidin-1-yl}-pyrimidin-5-yl)-methanol;

4-Amino-6-{4-[4-(4-fluoro-3-trifluoromethyl-phenyl)-1-methyl-1H-imidazol-2-yl]-piperidin-1-yl}-pyrimidine-5-carboxamide;

4-Amino-6-{4-[1-(2-dimethylamino-ethyl)-4-(4-fluoro-3-trifluoromethyl-phenyl)-1H -imidazol-2-yl]-piperidin-1-yl}-pyrimidine-5-carboxylic acid amide;

6-{4-[4-(4-Fluoro-3-trifluoromethyl-phenyl)-1-methyl-1H-imidazol-2-yl]-piperidin-1-yl}-5-pyridin-4-yl-pyrimidin-4-ylamine;

5-(6-Amino-pyridin-3-yl)-6-{4-[4-(4-fluoro-3-trifluoromethyl-phenyl)-1-methyl-1H-imidazol-2-yl]-piperidin-1-yl}-pyrimidin-4-ylamine;

5-Bromo-4-{4-[4-(4-fluoro-3-trifluoromethyl-phenyl)-1-methyl-1H-imidazol-2-yl]-piperidin-1-yl}-pyrimidine;

5-(4-Fluoro-phenyl)-4-{4-[4-(4-fluoro-3-trifluoromethyl-phenyl)-1-methyl-1H-imidazol-2-yl]-piperidin-1-yl}-pyrimidine;

5-Bromo-6-{4-[4-(4-fluoro-3-trifluoromethyl-phenyl)-1H-imidazol-2-yl]-piperidin-1-yl}-pyrimidin-4-ylamine;

5-(4-Fluoro-phenyl)-6-{4-[4-(4-fluoro-3-trifluoromethyl-phenyl)-1H-imidazol-2-yl]-piperidin-1-yl}-pyrimidin-4-ylamine;

(E)-3-(4-Amino-6-{4-[4-(4-fluoro-3-trifluoromethyl-phenyl)-1-methyl-1H-imidazol-2-yl]-piperidin-1-yl}-pyrimidin-5-yl)-acrylic acid methyl ester;

(E)-3-(4-Amino-6-{4-[4-(4-fluoro-3-trifluoromethyl-phenyl)-1-methyl-1H-imidazol-2-yl]-piperidin-1-yl}-pyrimidin-5-yl)-acrylamide;

6-{4-[4-(4-Fluoro-3-trifluoromethyl-phenyl)-1-methyl-1H-imidazol-2-yl]-piperidin-1-yl}-5-(5-methoxy-pyridin-3-yl)-pyrimidin-4-ylamine;

6-{4-[4-(4-Fluoro-3-trifluoromethyl-phenyl)-1-methyl-1H-imidazol-2-yl]-piperidin-1-yl}-[5,5']bipyrimidinyl-4-ylamine;

6-{4-[4-(4-Fluoro-3-trifluoromethyl-phenyl)-1-methyl-1H-imidazol-2-yl]-piperidin-1-yl}-5-(1H-indol-5-yl)-pyrimidin-4-ylamine;

5-(6-Chloro-pyridin-3-yl)-6-{4-[4-(4-fluoro-3-trifluoromethyl-phenyl)-1-methyl-1H-imidazol-2-yl]-piperidin-1-yl}-pyrimidin-4-ylamine;

5-(3-Chloro-phenyl)-6-{4-[4-(4-fluoro-3-trifluoromethyl-phenyl)-1-methyl-1H-imidazol-2-yl]-piperidin-1-yl}-pyrimidin-4-ylamine;

4-(4-Amino-6-{4-[4-(4-fluoro-3-trifluoromethyl-phenyl)-1-methyl-1H-imidazol-2-yl]-piperidin-1-yl}-pyrimidin-5-yl)-2-fluoro-benzonitrile;

6-{4-[4-(4-Fluoro-3-trifluoromethyl-phenyl)-1-methyl-1H-imidazol-2-yl]-piperidin-1-yl}-5-pyridin-3-yl-pyrimidin-4-ylamine;

6-{4-[4-(4-Fluoro-3-trifluoromethyl-phenyl)-1-methyl-1H-imidazol-2-yl]-piperidin-1-yl}-5-((E)-3-methoxy-propenyl)-pyrimidin-4-ylamine;

6-{4-[4-(4-Fluoro-3-trifluoromethyl-phenyl)-1-methyl-1H-imidazol-2-yl]-piperidin-1-yl}-5-(2-methyl-thiazol-5-yl)-pyrimidin-4-ylamine;

5-Bromo-6-{4-[4-(4-fluoro-3-trifluoromethyl-phenyl)-1-2-pyrrolidin-1-yl-ethyl)-1H-imidazol-2-yl]-piperidin-1-yl}-pyrimidin-4-ylamine;

5-(4-Fluorophenyl)-6-{4-(4-fluoro-3-trifluoromethyl-phenyl)-1-2-pyrrolidin-1-yl-ethyl)-1H-imidazol-2-yl]-piperidin-1-yl}-pyrimidin-4-ylamine;

5-(2-Fluorophenyl)-6-{4-(4-fluoro-3-trifluoromethyl-phenyl)-1-2-pyrrolidin-1-yl-ethyl)-1H-imidazol-2-yl]-piperidin-1-yl}-pyrimidin-4-ylamine;

5-(3,4-Difluorophenyl)-6-{4-(4-fluoro-3-trifluoromethyl-phenyl)-1-2-pyrrolidin-1-yl-ethyl)-1H-imidazol-2-yl]-piperidin-1-yl}-pyrimidin-4-ylamine;

6-{4-(4-fluoro-3-trifluoromethyl-phenyl)-1-2-pyrrolidin-1-yl-ethyl)-1H-imidazol-2-yl]-piperidin-1-yl}-5-vinyl-pyrimidin-4-ylamine;

5-Bromo-6-{4-[4-(4-fluoro-3-trifluoromethyl-phenyl)-1-(2-piperidin-1-yl-ethyl)-1H-imidazol-2-yl]-piperidin-1-yl}-pyrimidin-4-ylamine;

5-(4-Fluorophenyl)-6-{4-(4-fluoro-3-trifluoromethyl-phenyl)-1-2-piperidin-1-yl-ethyl)-1H-imidazol-2-yl]-piperidin-1-yl}-pyrimidin-4-ylamine;

5-(2-Fluorophenyl)-6-{4-(4-fluoro-3-trifluoromethyl-phenyl)-1-2-piperidin-1-yl-ethyl)-1H-imidazol-2-yl]-piperidin-1-yl}-pyrimidin-4-ylamine;

5-(3-Fluorophenyl)-6-{4-(4-fluoro-3-trifluoromethyl-phenyl)-1-2-piperidin-1-yl-ethyl)-1H-imidazol-2-yl]-piperidin-1-yl}-pyrimidin-4-ylamine;

6-{4-[4-(4-Fluoro-3-trifluoromethyl-phenyl)-1-(2-piperidin-1-yl-ethyl)-1H-imidazol-2-yl]-piperidin-1-yl}-5-vinyl-pyrimidin-4-ylamine;

6-{4-(4-fluoro-3-trifluoromethyl-phenyl)-1-2-piperidin-1-yl-ethyl)-1H-imidazol-2-yl]-piperidin-1-yl}-pyrimidin-4-ylamine;

5-Bromo-6-{4-[1-(2-dimethylamino-ethyl)-4-(4-fluoro-3-trifluoromethyl-phenyl)-1H-imidazol-2-yl]-piperidin-1-yl}-pyrimidin-4-ylamine;

6-{4-[1-(2-Dimethylamino-ethyl)-4-(4-fluoro-3-trifluoromethyl-phenyl)-1H-imidazol-2-yl]-piperidin-1-yl}-5-(4-fluoro-phenyl)-pyrimidin-4-ylamine;

6-{4-[1-(2-Dimethylamino-ethyl)-4-(4-fluoro-3-trifluoromethyl-phenyl)-1H-imidazol-2-yl]-piperidin-1-yl}-5-pyridin-4-yl-pyrimidin-4-ylamine;

6-{4-[1-(2-Dimethylamino-ethyl)-4-(4-fluoro-3-trifluoromethyl-phenyl)-1H-imidazol-2-yl]-piperidin-1-yl}-5-pyridin-4-yl-pyrimidin-4-ylamine;

6'-{4-[1-(2-Dimethylamino-ethyl)-4-(4-fluoro-3-trifluoromethyl-phenyl)-1H-imidazol-2-yl]-piperidin-1-yl}-[5,5']bipyrimidinyl-2,4'-diamine;

6-{4-[1-(2-Dimethylamino-ethyl)-4-(4-fluoro-3-trifluoromethyl-phenyl)-1H-imidazol-2-yl]-piperidin-1-yl}-5-isopropenyl-pyrimidin-4-ylamine;

6-{4-[1-(2-Dimethylamino-ethyl)-4-(4-fluoro-3-trifluoromethyl-phenyl)-1H-imidazol-2-yl]-piperidin-1-yl}-5-vinyl-pyrimidin-4-ylamine;

4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carbonitrile;
4-Amino-6-{4-[1-(2-azetidin-1-yl-ethyl)-4-(3-chloro-4-fluoro-phenyl)-1H-imidazol-2-yl]-piperidin-1-yl}-pyrimidine-5-carbonitrile;
4-Amino-6-{4-[1-(2-azetidin-1-yl-ethyl)-4-(4-difluoromethoxy-phenyl)-1H-imidazol-2-yl]-piperidin-1-yl}-pyrimidine-5-carbonitrile;
4-Amino-6-{4-[1-(2-azetidin-1-yl-ethyl)-4-cyclohexyl-1H-imidazol-2-yl]-piperidin-1-yl}-pyrimidine-5-carbonitrile;
4-Amino-6-{4-[1-(2-azetidin-1-yl-ethyl)-4-(4-fluoro-3-trifluoromethyl-phenyl)-1H-imidazol-2-yl]-piperidin-1-yl}-pyrimidine-5-carboxylic acid amide;
4-Amino-6-{4-[1-(2-azetidin-1-yl-ethyl)-4-(3-chloro-4-fluoro-phenyl)-1H-imidazol-2-yl]-piperidin-1-yl}-pyrimidine-5-carboxylic acid amide;
4-Amino-6-{4-[1-(2-azetidin-1-yl-ethyl)-4-cyclohexyl-1H-imidazol-2-yl]-piperidin-1-yl}-pyrimidine-5-carboxylic acid amide;
4-Amino-6-{4-[1-(2-azetidin-1-yl-ethyl)-4-(4-difluoromethoxy-phenyl)-1H-imidazol-2-yl]-piperidin-1-yl}-pyrimidine-5-carboxylic acid amide;
6-(4-(1-(2-(Dimethylamino)ethyl)-4-(4-fluoro-3-(trifluoromethyl)phenyl)-1H-imidazol-2-yl)piperidin-1-yl)-5-ethylpyrimidin-4-amine;
5-(2-Cyclopropylethyl)-6-(4-(1-(2-(dimethylamino)ethyl)-4-(4-fluoro-3-(trifluoromethyl)phenyl)-1H-imidazol-2-yl)piperidin-1-yl)pyrimidin-4-amine;
6-(4-(1-(2-(Dimethylamino)ethyl)-4-(4-fluoro-3-(trifluoromethyl)phenyl)-1H-imidazol-2-yl)piperidin-1-yl)-5-(2-ethoxyethyl)pyrimidin-4-amine;
(E)-5-(2-Cyclopropylvinyl)-6-(4-(1-(2-(dimethylamino)ethyl)-4-(4-fluoro-3-(trifluoromethyl)phenyl)-1H-imidazol-2-yl)piperidin-1-yl)pyrimidin-4-amine;
(E)-6-(4-(1-(2-(Dimethylamino)ethyl)-4-(4-fluoro-3-(trifluoromethyl)phenyl)-1H-imidazol-2-yl)piperidin-1-yl)-5-(2-ethoxyvinyl)pyrimidin-4-amine;
2-(4-(4-Amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)phenyl)propan-2-ol;
Methyl 4-(4-amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)benzoate;
4-(4-Amino-6-(4-(1-(2-(dimethylamino)ethyl)-4-(4-fluoro-3-(trifluoromethyl)phenyl)-1H-imidazol-2-yl)piperidin-1-yl)pyrimidin-5-yl)benzoic acid;
5-(Cyclopent-1-en-1-yl)-6-(4-(1-(2-(dimethylamino)ethyl)-4-(4-fluoro-3-(trifluoromethyl)phenyl)-1H-imidazol-2-yl)piperidin-1-yl)pyrimidin-4-amine;
5-Cyclopropyl-6-(4-(1-(2-(dimethylamino)ethyl)-4-(4-fluoro-3-(trifluoromethyl)phenyl)-1H-imidazol-2-yl)piperidin-1-yl)pyrimidin-4-amine;
5-ethyl-6-(4-(4-(4-fluoro-3-(trifluoromethyl)phenyl)-1-(2-(3-fluoroazetidin-1-yl)ethyl)-1H-imidazol-2-yl)piperidin-1-yl)pyrimidin-4-amine;
5-ethyl-6-(4-(4-(4-fluoro-3-(trifluoromethyl)phenyl)-1-(2-(3-methylazetidin-1-yl)ethyl)-1H-imidazol-2-yl)piperidin-1-yl)pyrimidin-4-amine;
6-(4-(1-(2-(3,3-difluoroazetidin-1-yl)ethyl)-4-(4-fluoro-3-(trifluoromethyl)phenyl)-1H-imidazol-2-yl)piperidin-1-yl)-5-ethylpyrimidin-4-amine;
6-(4-(1-(2-(dimethylamino)ethyl)-4-(4-fluoro-3-(trifluoromethyl)phenyl)-1H-imidazol-2-yl)piperidin-1-yl)-5-((ethyl(methylamino)methyl)pyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-isopropoxypyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-methoxypyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-(1H-pyrazol-4-yl)pyrimidin-4-amine;
6-(4-(1-(2-(azetidin-1-yl)ethyl)-4-(5-(trifluoromethyl)pyridin-3-yl)-1H-imidazol-2-yl)piperidin-1-yl)-5-ethylpyrimidin-4-amine;
6-(4-(1-(2-(azetidin-1-yl)ethyl)-4-(3-(trifluoromethoxy)phenyl)-1H-imidazol-2-yl)piperidin-1-yl)-5-ethylpyrimidin-4-amine;
6-(4-(1-(2-(azetidin-1-yl)ethyl)-4-(5-chloropyridin-3-yl)-1H-imidazol-2-yl)piperidin-1-yl)-5-ethylpyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-ethoxypyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-(2,2,2-trifluoroethoxyl)pyrimidin-4-amine;
6-(4-(1-(2-(azetidin-1-yl)ethyl)-4-(2-chloropyridin-4-yl)-1H-imidazol-2-yl)piperidin-1-yl)-5-ethylpyrimidin-4-amine;
6-(4-(1-(2-(azetidin-1-yl)ethyl)-4-(2-(trifluoromethyl)pyridin-4-yl)-1H-imidazol-2-yl)piperidin-1-yl)-5-ethylpyrimidin-4-amine;
5-(2-(1-(6-amino-5-ethylpyrimidin-4-yl)piperidin-4-yl)-1-(2-(azetidin-1-yl)ethyl)-1H-imidazol-4-yl)-2-fluorobenzamide;
5-(2-(1-(6-amino-5-ethylpyrimidin-4-yl)piperidin-4-yl)-1-(2-(azetidin-1-yl)ethyl)-1H-imidazol-4-yl)-2-methoxybenzamide;
6-(4-(1-(2-(azetidin-1-yl)ethyl)-4-(4-fluoro-3-methoxyphenyl)-1H-imidazol-2-yl)piperidin-1-yl)-5-ethylpyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-(isoxazol-4-yl)pyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-(1H-pyrrol-3-yl)pyrimidin-4-amine;
6-(4-(1-(2-(azetidin-1-yl)ethyl)-4-(2-methylpyridin-4-yl)-1H-imidazol-2-yl)piperidin-1-yl)-5-ethylpyrimidin-4-amine;
6-(4-(1-(2-(azetidin-1-yl)ethyl)-4-(2-methoxypyridin-4-yl)-1H-imidazol-2-yl)piperidin-1-yl)-5-ethylpyrimidin-4-amine;
6-(4-(1-(2-(azetidin-1-yl)ethyl)-4-(5-methylpyridin-3-yl)-1H-imidazol-2-yl)piperidin-1-yl)-5-ethylpyrimidin-4-amine;
6-(4-(1-(2-(azetidin-1-yl)ethyl)-4-(4-fluoro-3-(trifluoromethyl)phenyl)-1H-imidazol-2-yl)piperidin-1-yl)-5-isopropylpyrimidin-4-amine;
6-(4-(1-(2-(azetidin-1-yl)ethyl)-4-(2-(trifluoromethyl)pyridin-4-yl)-1H-imidazol-2-yl)piperidin-1-yl)-5-methoxypyrimidin-4-amine;
6-(4-(1-(2-(azetidin-1-yl)ethyl)-4-(2-(trifluoromethyl)pyridin-4-yl)-1H-imidazol-2-yl)piperidin-1-yl)-5-ethoxypyrimidin-4-amine;
6-(4-(1-(2-(azetidin-1-yl)ethyl)-4-(2-(trifluoromethyl)pyridin-4-yl)-1H-imidazol-2-yl)piperidin-1-yl)-5-isopropoxypyrimidin-4-amine;

6-(4-(1-(2-(azetidin-1-yl)ethyl)-4-(2-(trifluoromethyl)pyridin-4-yl)-1H-imidazol-2-yl)piperidin-1-yl)-5-(2,2,2-trifluoroethoxy)pyrimidin-4-amine;

6-(4-(1-(2-(azetidin-1-yl)ethyl)-4-(6-(trifluoromethyl)pyridin-2-yl)-1H-imidazol-2-yl)piperidin-1-yl)-5-ethylpyrimidin-4-amine;

4-amino-6-(4-(1-(2-(azetidin-1-yl)ethyl)-4-(4-fluoro-3-methoxyphenyl)-1H-imidazol-2-yl)piperidin-1-yl)pyrimidine-5-carbonitrile;

4-amino-6-(4-(1-(2-(azetidin-1-yl)ethyl)-4-(4-fluoro-3-methoxyphenyl)-1H-imidazol-2-yl)piperidin-1-yl)pyrimidine-5-carboxamide;

4-amino-6-(4-(1-(2-(azetidin-1-yl)ethyl)-4-(4-fluoro-3-methylphenyl)-1H-imidazol-2-yl)piperidin-1-yl)pyrimidine-5-carbonitrile;

6-(4-(1-(2-(azetidin-1-yl)ethyl)-4-(6-chloropyridin-2-yl)-1H-imidazol-2-yl)piperidin-1-yl)-5-ethylpyrimidin-4-amine;

4-amino-6-(4-(1-(2-(azetidin-1-yl)ethyl)-4-(4-fluoro-3-methylphenyl)-1H-imidazol-2-yl)piperidin-1-yl)pyrimidine-5-carboxamide;

4-amino-6-(4-(1-(2-(azetidin-1-yl)ethyl)-4-(2-(trifluoromethyl)pyridin-4-yl)-1H-imidazol-2-yl)piperidin-1-yl)pyrimidine-5-carbonitrile;

6-(4-(1-(2-(azetidin-1-yl)ethyl)-4-(2-(trifluoromethyl)pyridin-4-yl)-1H-imidazol-2-yl)piperidin-1-yl)-5-bromopyrimidin-4-amine;

5-bromo-6-(4-(1-(2-((3-chloropropyl)amino)ethyl)-4-(2-(trifluoromethyl)pyridin-4-yl)-1H-imidazol-2-yl)piperidin-1-yl)pyrimidin-4-amine;

4-amino-6-(4-(1-(2-aminoethyl)-4-(2-(trifluoromethyl)pyridin-4-yl)-1H-imidazol-2-yl)piperidin-1-yl)pyrimidine-5-carboxylic acid;

4-amino-6-(4-(1-(2-(azetidin-1-yl)ethyl)-4-(furan-3-yl)-1H-imidazol-2-yl)piperidin-1-yl)pyrimidine-5-carbonitrile;

4-amino-6-(4-(1-(2-(azetidin-1-yl)ethyl)-4-(thiophen-3-yl)-1H-imidazol-2-yl)piperidin-1-yl)pyrimidine-5-carbonitrile;

4-amino-6-(4-(1-(2-(azetidin-1-yl)ethyl)-4-phenyl-1H-imidazol-2-yl)piperidin-1-yl)pyrimidine-5-carbonitrile;

4-amino-6-(4-(1-(2-(azetidin-1-yl)ethyl)-4-(isoxazol-4-yl)-1H-imidazol-2-yl)piperidin-1-yl)pyrimidine-5-carbonitrile;

4-amino-6-(4-(1-(2-(azetidin-1-yl)ethyl)-4-(furan-3-yl)-1H-imidazol-2-yl)piperidin-1-yl)pyrimidine-5-carboxamide;

4-amino-6-(4-(1-(2-(azetidin-1-yl)ethyl)-4-(thiophen-3-yl)-1H-imidazol-2-yl)piperidin-1-yl)pyrimidine-5-carboxamide;

4-amino-6-(4-(1-(2-(azetidin-1-yl)ethyl)-4-(isoxazol-4-yl)-1H-imidazol-2-yl)piperidin-1-yl)pyrimidine-5-carboxamide;

4-amino-6-(4-(1-(2-(azetidin-1-yl)ethyl)-4-phenyl-1H-imidazol-2-yl)piperidin-1-yl)pyrimidine-5-carboxamide;

4-amino-6-(4-(4-(4-fluoro-3-(trifluoromethyl)phenyl)-1-(pyrrolidin-3-yl)-1H-imidazol-2-yl)piperidin-1-yl)pyrimidine-5-carbonitrile;

4-amino-6-(4-(4-(4-fluoro-3-(trifluoromethyl)phenyl)-1-(pyrrolidin-3-yl)-1H-imidazol-2-yl)piperidin-1-yl)pyrimidine-5-carboxamide;

6-(4-(1-(2-aminoethyl)-4-(4-fluoro-3-(trifluoromethyl)phenyl)-1H-imidazol-2-yl)piperidin-1-yl)-5-ethylpyrimidin-4-amine;

4-amino-6-(4-(1-(azetidin-3-ylmethyl)-4-(4-fluoro-3-(trifluoromethyl)phenyl)-1H-imidazol-2-yl)piperidin-1-yl)pyrimidine-5-carboxamide;

4-amino-6-(4-(1-(azetidin-3-ylmethyl)-4-(4-fluoro-3-(trifluoromethyl)phenyl)-1H-imidazol-2-yl)piperidin-1-yl)pyrimidine-5-carbonitrile;

4-amino-6-(4-(1-(azetidin-3-yl)-4-(4-fluoro-3-(trifluoromethyl)phenyl)-1H-imidazol-2-yl)piperidin-1-yl)pyrimidine-5-carbonitrile;

4-amino-6-(4-(1-(azetidin-3-yl)-4-(4-fluoro-3-(trifluoromethyl)phenyl)-1H-imidazol-2-yl)piperidin-1-yl)pyrimidine-5-carboxamide;

6-(4-(1-(2-(azetidin-1-yl)ethyl)-4-(2-(trifluoromethyl)pyridin-4-yl)-1H-imidazol-2-yl)piperidin-1-yl)-5-chloropyrimidin-4-amine;

4-amino-6-(4-(1-(2-(azetidin-1-yl)ethyl)-4-(1H-pyrazol-4-yl)-1H-imidazol-2-yl)piperidin-1-yl)pyrimidine-5-carboxamide;

(S)-4-amino-6-(4-(1-(azetidin-2-ylmethyl)-4-(4-fluoro-3-(trifluoromethyl)phenyl)-1H-imidazol-2-yl)piperidin-1-yl)pyrimidine-5-carbonitrile;

4-amino-6-(4-(4-(4-fluoro-3-(trifluoromethyl)phenyl)-1-(pyrrolidin-2-ylmethyl)-1H-imidazol-2-yl)piperidin-1-yl)pyrimidine-5-carbonitrile;

6-(4-(1-(azetidin-3-ylmethyl)-4-(4-fluoro-3-(trifluoromethyl)phenyl)-1H-imidazol-2-yl)piperidin-1-yl)-5-chloropyrimidin-4-amine;

(S)-6-(4-(1-(azetidin-2-ylmethyl)-4-(4-fluoro-3-(trifluoromethyl)phenyl)-1H-imidazol-2-yl)piperidin-1-yl)-5-chloropyrimidin-4-amine;

(S)-4-amino-6-(4-(1-(azetidin-2-ylmethyl)-4-(4-fluoro-3-(trifluoromethyl)phenyl)-1H-imidazol-2-yl)piperidin-1-yl)pyrimidine-5-carboxamide;

6-(4-(1-(azetidin-3-ylmethyl)-4-(4-fluoro-3-(trifluoromethyl)phenyl)-1H-imidazol-2-yl)piperidin-1-yl)-5-ethylpyrimidin-4-amine;

(S)-6-(4-(1-(azetidin-2-ylmethyl)-4-(4-fluoro-3-(trifluoromethyl)phenyl)-1H-imidazol-2-yl)piperidin-1-yl)-5-ethylpyrimidin-4-amine;

4-amino-6-(4-(4-(4-fluoro-3-(trifluoromethyl)phenyl)-1-(pyrrolidin-2-ylmethyl)-1H-imidazol-2-yl)piperidin-1-yl)pyrimidine-5-carboxamide;

4-amino-6-(4-(4-(4-fluoro-3-(trifluoromethyl)phenyl)-1-(piperidin-4-yl)-1H-imidazol-2-yl)piperidin-1-yl)pyrimidine-5-carboxamide;

4-amino-6-(4-(4-(4-fluoro-3-(trifluoromethyl)phenyl)-1-(piperidin-4-yl)-1H-imidazol-2-yl)piperidin-1-yl)pyrimidine-5-carbonitrile;

4-amino-6-(4-(4-(4-fluoro-3-(trifluoromethyl)phenyl)-1-((1-methylazetidin-3-yl)methyl)-1H-imidazol-2-yl)piperidin-1-yl)pyrimidine-5-carboxamide;

5-ethyl-6-(4-(4-(4-fluoro-3-(trifluoromethyl)phenyl)-1-(piperidin-4-yl)-1H-imidazol-2-yl)piperidin-1-yl)pyrimidin-4-amine;

4-amino-6-(4-(1-(2-aminoethyl)-4-(4-fluoro-3-(trifluoromethyl)phenyl)-1H-imidazol-2-yl)piperidin-1-yl)pyrimidine-5-carbonitrile;

4-amino-6-(4-(1-(2-aminoethyl)-4-(4-fluoro-3-(trifluoromethyl)phenyl)-1H-imidazol-2-yl)piperidin-1-yl)pyrimidine-5-carboxamide;

2-(2-(1-(6-amino-5-(1H-pyrazol-4-yl)pyrimidin-4-yl)piperidin-4-yl)-4-(4-fluoro-3-methylphenyl)-1H-imidazol-1-yl)ethanol;

6-(4-(1-(2-(cyclopropylamino)ethyl)-4-(4-fluoro-3-methylphenyl)-1H-imidazol-2-yl)piperidin-1-yl)-5-(1H-pyrazol-4-yl)pyrimidin-4-amine;

6-(4-(4-(4-fluoro-3-methylphenyl)-1-(2-(methylamino)ethyl)-1H-imidazol-2-yl)piperidin-1-yl)-5-(1H-pyrazol-4-yl)pyrimidin-4-amine;

6-(4-(1-(2-(dimethylamino)ethyl)-4-(4-fluoro-3-methylphenyl)-1H-imidazol-2-yl)piperidin-1-yl)-5-(1H-pyrazol-4-yl)pyrimidin-4-amine;

6-(4-(1-(2-(azetidin-1-yl)ethyl)-4-(4-fluoro-3-methylphenyl)-1H-imidazol-2-yl)piperidin-1-yl)-5-(1H-pyrazol-4-yl)pyrimidin-4-amine;

6-(4-(1-(2-(tert-butylamino)ethyl)-4-(4-fluoro-3-methylphenyl)-1H-imidazol-2-yl)piperidin-1-yl)-5-(1H-pyrazol-4-yl)pyrimidin-4-amine;

5-bromo-6-(4-(1-(2-(methylamino)ethyl)-4-(2-(trifluoromethyl)pyridin-4-yl)-1H-imidazol-2-yl)piperidin-1-yl)pyrimidin-4-amine;

6-(4-(1-(2-(methylamino)ethyl)-4-(2-(trifluoromethyl)pyridin-4-yl)-1H-imidazol-2-yl)piperidin-1-yl)pyrimidin-4-amine;

6-(4-(1-(2-(azetidin-1-yl)ethyl)-4-(2-(trifluoromethyl)pyridin-4-yl)-1H-imidazol-2-yl)piperidin-1-yl)-5-(isoxazol-4-yl)pyrimidin-4-amine;

4-amino-6-(4-(1-(2-(methylamino)ethyl)-4-(2-(trifluoromethyl)pyridin-4-yl)-1H-imidazol-2-yl)piperidin-1-yl)pyrimidine-5-carbonitrile;

5-(4,5-dihydroisoxazol-4-yl)-6-(4-(1-(2-(methylamino)ethyl)-4-(2-(trifluoromethyl)pyridin-4-yl)-1H-imidazol-2-yl)piperidin-1-yl)pyrimidin-4-amine;

5-ethyl-6-(4-(1-(2-(methylamino)ethyl)-4-(2-(trifluoromethyl)pyridin-4-yl)-1H-imidazol-2-yl)piperidin-1-yl)pyrimidin-4-amine;

5-chloro-6-(4-(1-(2-(methylamino)ethyl)-4-(2-(trifluoromethyl)pyridin-4-yl)-1H-imidazol-2-yl)piperidin-1-yl)pyrimidin-4-amine;

5-chloro-6-(4-(1-(2-(cyclopropylamino)ethyl)-4-(2-(trifluoromethyl)pyridin-4-yl)-1H-imidazol-2-yl)piperidin-1-yl)pyrimidin-4-amine;

6-(4-(1-(2-(ethylamino)ethyl)-4-(4-fluoro-3-(trifluoromethyl)phenyl)-1H-imidazol-2-yl)piperidin-1-yl)-5-isopropoxypyrimidin-4-amine;

6-(4-(1-(azetidin-3-ylmethyl)-4-(4-fluoro-3-(trifluoromethyl)phenyl)-1H-imidazol-2-yl)piperidin-1-yl)-5-isopropoxypyrimidin-4-amine;

6-(4-(1-(azetidin-3-ylmethyl)-4-(4-fluoro-3-(trifluoromethyl)phenyl)-1H-imidazol-2-yl)piperidin-1-yl)-5-ethoxypyrimidin-4-amine;

6-(4-(1-(2-(azetidin-1-yl)ethyl)-4-(4-fluoro-3-(trifluoromethyl)phenyl)-1H-imidazol-2-yl)piperidin-1-yl)-5-ethoxypyrimidin-4-amine;

6-(4-(1-(2-(azetidin-1-yl)ethyl)-4-(4-fluoro-3-methylphenyl)-1H-imidazol-2-yl)piperidin-1-yl)-5-isopropoxypyrimidin-4-amine;

6-(4-(1-(2-(azetidin-1-yl)ethyl)-4-(2-isopropylpyridin-4-yl)-1H-imidazol-2-yl)piperidin-1-yl)-5-ethylpyrimidin-4-amine;

6-(4-(1-(2-(azetidin-1-yl)ethyl)-4-(2-isopropylpyridin-4-yl)-1H-imidazol-2-yl)piperidin-1-yl)-5-chloropyrimidin-4-amine;

6-(4-(1-(2-(azetidin-1-yl)ethyl)-4-(2-isopropylpyridin-4-yl)-1H-imidazol-2-yl)piperidin-1-yl)-5-bromopyrimidin-4-amine;

6-(4-(1-(2-(azetidin-1-yl)ethyl)-4-(2-isopropylpyridin-4-yl)-1H-imidazol-2-yl)piperidin-1-yl)-5-vinylpyrimidin-4-amine;

6-(4-(1-(azetidin-3-ylmethyl)-4-(4-fluoro-3-(trifluoromethyl)phenyl)-1H-imidazol-2-yl)piperidin-1-yl)-5-vinylpyrimidin-4-amine;

6-(4-(1-(azetidin-3-ylmethyl)-4-(4-fluoro-3-methylphenyl)-1H-imidazol-2-yl)piperidin-1-yl)-5-methoxypyrimidin-4-amine;

6-(4-(1-(azetidin-3-ylmethyl)-4-(4-fluoro-3-methylphenyl)-1H-imidazol-2-yl)piperidin-1-yl)-5-ethoxypyrimidin-4-amine;

6-(4-(1-(azetidin-3-ylmethyl)-4-(4-fluoro-3-methylphenyl)-1H-imidazol-2-yl)piperidin-1-yl)-5-(2,2,2-trifluoroethoxyl)pyrimidin-4-amine;

6-(4-(1-(azetidin-3-ylmethyl)-4-(4-fluoro-3-methylphenyl)-1H-imidazol-2-yl)piperidin-1-yl)-5-isopropoxypyrimidin-4-amine;

6-(4-(1-(azetidin-3-ylmethyl)-4-(4-fluoro-3-methylphenyl)-1H-imidazol-2-yl)piperidin-1-yl)-5-ethylpyrimidin-4-amine;

6-(4-(1-(azetidin-3-ylmethyl)-4-(4-fluoro-3-methylphenyl)-1H-imidazol-2-yl)piperidin-1-yl)-5-isopropylpyrimidin-4-amine;

6-(4-(1-(2-(azetidin-1-yl)ethyl)-4-(4-fluoro-3-methylphenyl)-1H-imidazol-2-yl)piperidin-1-yl)-5-bromopyrimidin-4-amine;

4-amino-6-(4-(1-(azetidin-3-ylmethyl)-4-(4-fluoro-3-methylphenyl)-1H-imidazol-2-yl)piperidin-1-yl)pyrimidine-5-carbonitrile;

6-(4-(1-(2-(azetidin-1-yl)ethyl)-4-(2-(trifluoromethyl)pyridin-4-yl)-1H-imidazol-2-yl)piperidin-1-yl)-5-chloro-N-methylpyrimidin-4-amine;

(6-{4-[1-Azetidin-3-ylmethyl-4-(4-fluoro-3-methyl-phenyl)-1H-imidazol-2-yl]-piperidin-1-yl}-5-chloro-pyrimidin-4-yl)-methyl-amine;

6-(4-(1-(azetidin-3-ylmethyl)-4-(4-fluoro-3-methylphenyl)-1H-imidazol-2-yl)cyclohexyl)-5-isopropylpyrimidin-4-amine;

5-Ethyl-6-{4-[4-(4-fluoro-phenyl)-1-(2-morpholin-4-yl-ethyl)-1H-imidazol-2-yl]-piperidin-1-yl}-pyrimidin-4-ylamine;

6-{4-[4-(3,4-Difluoro-phenyl)-1-(2-morpholin-4-yl-ethyl)-1H-imidazol-2-yl]-piperidin-1-yl}-5-ethyl-pyrimidin-4-ylamine;

5-Ethyl-6-(4-{4-(4-fluoro-phenyl)-1-[2-(2-oxa-6-aza-spiro[3.3]hept-6-yl)-ethyl]-1H-imidazol-2-yl}-piperidin-1-yl)-pyrimidin-4-ylamine;

6-(4-{4-(3,4-Difluoro-phenyl)-1-[2-(2-oxa-6-aza-spiro[3.3]hept-6-yl)-ethyl]-1H-imidazol-2-yl}-piperidin-1-yl)-5-ethyl-pyrimidin-4-ylamine;

6-(4-{4-(3,4-Difluoro-phenyl)-1-[2-(3-fluoro-azetidin-1-yl)-ethyl]-1H-imidazol-2-yl}-piperidin-1-yl)-5-ethyl-pyrimidin-4-ylamine;

5-Ethyl-6-{4-[1-[2-(3-fluoro-azetidin-1-yl)-ethyl]-4-(4-fluoro-phenyl)-1H-imidazol-2-yl]-piperidin-1-yl}-pyrimidin-4-ylamine;

5-Ethyl-6-(4-{4-(4-fluoro-phenyl)-1-[2-(2-oxa-6-aza-spiro[3.4]oct-6-yl)-ethyl]-1H-imidazol-2-yl}-piperidin-1-yl)-pyrimidin-4-ylamine;

6-(4-{4-(3,4-Difluoro-phenyl)-1-[2-(2-oxa-6-aza-spiro[3.4]oct-6-yl)-ethyl]-1H-imidazol-2-yl}-piperidin-1-yl)-5-ethyl-pyrimidin-4-ylamine;

6-(4-{4-(3,4-Difluoro-phenyl)-1-[2-(6-oxa-1-aza-spiro[3.3]hept-1-yl)-ethyl]-1H-imidazol-2-yl}-piperidin-1-yl)-5-ethyl-pyrimidin-4-ylamine;

5-Ethyl-6-(4-{4-(4-fluoro-phenyl)-1-[2-(6-oxa-1-aza-spiro[3.3]hept-1-yl)-ethyl]-1H-imidazol-2-yl}-piperidin-1-yl)-pyrimidin-4-ylamine;

4-Amino-6-{4-[1-(2-azetidin-1-yl-ethyl)-4-(5-chloro-6-fluoro-pyridin-3-yl)-1H-imidazol-2-yl]-piperidin-1-yl}-pyrimidine-5-carbonitrile;

4-Amino-6-{4-[1-(2-azetidin-1-yl-ethyl)-4-(2-fluoro-pyridin-4-yl)-1H-imidazol-2-yl]-piperidin-1-yl}-pyrimidine-5-carbonitrile;

4-Amino-6-{4-[1-(2-azetidin-1-yl-ethyl)-4-(1H-indazol-5-yl)-1H-imidazol-2-yl]-piperidin-1-yl}-pyrimidine-5-carbonitrile;

6-{4-(4-fluoro-3-trifluoromethyl-phenyl)-1-2-pyrrolidin-1-yl-ethyl)-1H-imidazol-2-yl]-piperidin-1-yl}-5-ethyl-pyrimidin-4-ylamine;

5-Chloro-6-{4-(4-fluoro-3-trifluoromethyl-phenyl)-1-2-pyrrolidin-1-yl-ethyl)-1H-imidazol-2-yl]-piperidin-1-yl}-pyrimidin-4-ylamine;

5-Chloro-6-{4-(4-hydroxy-3-trifluoromethyl-phenyl)-1-2-pyrrolidin-1-yl-ethyl)-1H-imidazol-2-yl]-piperidin-1-yl}-pyrimidin-4-ylamine;

5-Fluoro-6{4-(4-fluoro-3-trifluoromethyl-phenyl)-1-2-pyrrolidin-1-yl-ethyl)-1H-imidazol-2-yl]-piperidin-1-yl}-pyrimidin-4-ylamine;

6-{4-(4-fluoro-3-trifluoromethyl-phenyl)-1-2-piperidin-1-yl-ethyl)-1H-imidazol-2-yl]-piperidin-1-yl}-5-isopropylene-pyrimidin-4-ylamine;

6-{4-(4-fluoro-3-trifluoromethyl-phenyl)-1-2-pyrrolidin-1-yl-ethyl)-1H-imidazol-2-yl]-piperidin-1-yl}-5-isopropylene-pyrimidin-4-ylamine;

6-{4-(4-fluoro-3-trifluoromethyl-phenyl)-1-2-pyrrolidin-1-yl-ethyl)-1H-imidazol-2-yl]-piperidin-1-yl}-yrimidin-4-ylamine;

6-{4-(4-fluoro-3-trifluoromethyl-phenyl)-1-2-pyrrolidin-1-yl-ethyl)-1H-imidazol-2-yl]-piperidin-1-yl}-5-methyl-pyrimidin-4-ylamine;

5-Chloro-6-{4-(4-fluoro-3-trifluoromethyl-phenyl)-1-2-piperidin-1-yl-ethyl)-1H-imidazol-2-yl]-piperidin-1-yl}-pyrimidin-4-ylamine;

5-Bromo-6-{4-(4-fluoro-3-trifluoromethyl-phenyl)-1-2-pyrrolidin-1-yl-ethyl)-1H-imidazol-2-yl]-azetidin-1-yl}-pyrimidin-4-ylamine;

5-Chloro-6-{4-(4-fluoro-3-trifluoromethyl-phenyl)-1-2-pyrrolidin-1-yl-ethyl)-1H-imidazol-2-yl]-azetidin-1-yl}-pyrimidin-4-ylamine;

5-(4-fluorophenyl)-6-{4-(4-fluoro-3-trifluoromethyl-phenyl)-1-2-azetidin-1-yl-ethyl)-1H-imidazol-2-yl]-piperidin-1-yl}-pyrimidin-4-ylamine;

5-vinyl-6{4-(4-fluoro-3-trifluoromethyl-phenyl)-1-2-azetidin-1-yl-ethyl)-1H-imidazol-2-yl]-piperidin-1-yl}-pyrimidin-4-ylamine;

6-{4-(4-fluoro-3-trifluoromethyl-phenyl)-1-2-azetidin-1-yl-ethyl)-1H-imidazol-2-yl]-piperidin-1-yl}-pyrimidin-4-ylamine;

5-(4-methyl carboxylic ester-phenyl)-6-{4-(4-fluoro-3-trifluoromethyl-phenyl)-1-2-azetidin-1-yl-ethyl)-1H-imidazol-2-yl]-piperidin-1-yl}-pyrimidin-4-ylamine;

5-(4-methyl carboxylic ester-phenyl)-6-{4-(4-fluoro-3-trifluoromethyl-phenyl)-1-2-pyrrolidin-1-yl-ethyl)-1H-imidazol-2-yl]-piperidin-1-yl}-pyrimidin-4-ylamine;

5-(4-carboxylic acid-phenyl)-6-{4-(4-fluoro-3-trifluoromethyl-phenyl)-1-2-azetidin-1-yl-ethyl)-1H-imidazol-2-yl-piperidin-1-yl}-pyrimidin-4-ylamine;

5-(4-carboxylic acid-phenyl)-6-{4-(4-fluoro-3-trifluoromethyl-phenyl)-1-2-pyrrolidin-1-yl-ethyl)-1H-imidazol-2-yl-piperidin-1-yl}-pyrimidin-4-ylamine;

5-Bromo-6-{4-(3,4-difluorophenyl)-1-2-pyrrolidin-1-yl-ethyl)-1H-imidazol-2-yl]-piperidin-1-yl}-pyrimidin-4-ylamine;

5-Bromo-6-{4-(4-fluorophenyl)-1-2-pyrrolidin-1-yl-ethyl)-1H-imidazol-2-yl]-piperidin-1-yl}-pyrimidin-4-ylamine;

5-Bromo-6-{4-(3-fluorophenyl)-1-2-pyrrolidin-1-yl-ethyl)-1H-imidazol-2-yl]-piperidin-1-yl}-pyrimidin-4-ylamine;

5-Bromo-6-{4-(3-fluoro-4-trifluoromethylphenyl)-1-2-pyrrolidin-1-yl-ethyl)-1H-imidazol-2-yl]-piperidin-1-yl}-pyrimidin-4-ylamine;

5-Ethyl-6-{4-(4-fluoro-3-trifluoromethyl-phenyl)-1-2-azetidin-1-yl-ethyl)-1H-imidazol-2-yl]-piperidin-1-yl}-pyrimidin-4-ylamine;

5-Ethyl-6-{4-(3-fluorophenyl)-1-2-pyrrolidin-1-yl-ethyl)-1H-imidazol-2-yl]-piperidin-1-yl}-pyrimidin-4-ylamine;

5-Ethyl-6-{4-(4-fluorophenyl)-1-2-pyrrolidin-1-yl-ethyl)-1H-imidazol-2-yl]-piperidin-1-yl}-pyrimidin-4-ylamine;

5-Ethyl-6-{4-(3,4-difluorophenyl)-1-2-pyrrolidin-1-yl-ethyl)-1H-imidazol-2-yl]-piperidin-1-yl}-pyrimidin-4-ylamine;

5-Ethyl-6-{4-(3-fluoro-4-trifluoromethylphenyl)-1-2-pyrrolidin-1-yl-ethyl)-1H-imidazol-2-yl]-piperidin-1-yl}-pyrimidin-4-ylamine;

5-Chloro-6-{4-(3-fluoro-4-trifluoromethylphenyl)-1-2-pyrrolidin-1-yl-ethyl)-1H-imidazol-2-yl]-piperidin-1-yl}-pyrimidin-4-ylamine;

5-Chloro-6-{4-(3-fluoromethylphenyl)-1-2-pyrrolidin-1-yl-ethyl)-1H-imidazol-2-yl]-piperidin-1-yl}-pyrimidin-4-ylamine;

5-Chloro-6-{4-(4-fluoromethylphenyl)-1-2-pyrrolidin-1-yl-ethyl)-1H-imidazol-2-yl]-piperidin-1-yl}-pyrimidin-4-ylamine;

5-Chloro-6-{4-(3,4-difluoromethylphenyl)-1-2-pyrrolidin-1-yl-ethyl)-1H-imidazol-2-yl]-piperidin-1-yl}-pyrimidin-4-ylamine;

5-Vinyl-6-{4-(3-fluoro-4-trifluoromethylphenyl)-1-2-pyrrolidin-1-yl-ethyl)-1H-imidazol-2-yl]-piperidin-1-yl}-pyrimidin-4-ylamine;

5-Vinyl-6-{4-(3-fluorophenyl)-1-2-pyrrolidin-1-yl-ethyl)-1H-imidazol-2-yl]-piperidin-1-yl}-pyrimidin-4-ylamine;

5-Vinyl-6-{4-(4-fluorophenyl)-1-2-pyrrolidin-1-yl-ethyl)-1H-imidazol-2-yl]-piperidin-1-yl}-pyrimidin-4-ylamine;

5-Vinyl-6-{4-(3,4-difluorophenyl)-1-2-pyrrolidin-1-yl-ethyl)-1H-imidazol-2-yl]-piperidin-1-yl}-pyrimidin-4-ylamine;

6-{4-(3,4-difluorophenyl)-1-2-pyrrolidin-1-yl-ethyl)-1H-imidazol-2-yl]-piperidin-1-yl}-pyrimidin-4-ylamine;

6-{4-(3-fluorophenyl)-1-2-pyrrolidin-1-yl-ethyl)-1H-imidazol-2-yl]-piperidin-1-yl}-pyrimidin-4-ylamine;

5-Ethyl-6-{4-(3-fluoro-4-trifluoromethylphenyl)-1-2-((S)-3-fluoro-pyrrolidin-1-yl)-ethyl)-1H-imidazol-2-yl]-piperidin-1-yl}-pyrimidin-4-ylamine;

5-Ethyl-6-{4-(3-fluoro-4-trifluoromethylphenyl)-1-2-((R)-3-fluoro-pyrrolidin-1-yl)-ethyl)-1H-imidazol-2-yl]-piperidin-1-yl}-pyrimidin-4-ylamine;

5-Ethyl-6-{4-(3-fluoro-4-trifluoromethylphenyl)-1-2-(4,4-difluoro-piperidin-1-yl)-ethyl)-1H-imidazol-2-yl]-piperidin-1-yl}-pyrimidin-4-ylamine;

5-Ethyl-6-{4-(3-fluoro-4-trifluoromethylphenyl)-1-2-(3,3-difluoro-piperidin-1-yl)-ethyl)-1H-imidazol-2-yl]-piperidin-1-yl}-pyrimidin-4-ylamine;

5-Ethyl-6-{4-(3-fluoro-4-trifluoromethylphenyl)-1-2-(4-fluoro-piperidin-1-yl)-ethyl)-1H-imidazol-2-yl]-piperidin-1-yl}-pyrimidin-4-ylamine;

5-Ethyl-6-{4-(3-fluoro-4-trifluoromethylphenyl)-1-2-(3-fluoro-piperidin-1-yl)-ethyl)-1H-imidazol-2-yl]-piperidin-1-yl}-pyrimidin-4-ylamine;

5-Ethyl-6-{4-(3-fluoro-4-chlorophenyl)-1-2-(pyrrolidin-1-yl-ethyl)-1H-imidazol-2-yl]-piperidin-1-yl}-pyrimidin-4-ylamine;

5-Ethyl-6-{4-(4-fluoro-3-chlorophenyl)-1-2-(pyrrolidin-1-yl-ethyl)-1H-imidazol-2-yl]-piperidin-1-yl}-pyrimidin-4-ylamine;

5-cyclobutyl-6-{4-(3-fluoro-4-trifluoromethylphenyl)-1-2-(piperidin-1-yl-ethyl)-1H-imidazol-2-yl]-piperidin-1-yl}-pyrimidin-4-ylamine;

5-cyclobutyl-6-{4-(3-fluoro-4-trifluoromethylphenyl)-1-2-(pyrrolidin-1-yl-ethyl)-1H-imidazol-2-yl]-piperidin-1-yl}-pyrimidin-4-ylamine;

5-cyclobutyl-6-{4-(3,4-difluorophenyl)-1-2-(pyrrolidin-1-yl-ethyl)-1H-imidazol-2-yl]-piperidin-1-yl}-pyrimidin-4-ylamine;

5-cyclobutyl-6-{4-(4-fluorophenyl)-1-2-(pyrrolidin-1-yl-ethyl)-1H-imidazol-2-yl]-piperidin-1-yl}-pyrimidin-4-ylamine;

5-cyclobutyl-6-{4-(3-fluorophenyl)-1-2-(pyrrolidin-1-yl-ethyl)-1H-imidazol-2-yl]-piperidin-1-yl}-pyrimidin-4-ylamine;

5-cyclobutyl-6-{4-(3-fluoro-4-trifluoromethyl-phenyl)-1-2-(pyrrolidin-1-yl-ethyl)-1H-imidazol-2-yl]-piperidin-1-yl}-pyrimidin-4-ylamine;

5-cyclobutyl-6-{4-(4-trifluoromethyl-phenyl)-1-2-(pyrrolidin-1-yl-ethyl)-1H-imidazol-2-yl]-piperidin-1-yl}-pyrimidin-4-ylamine;

5-cyclobutyl-6-{4-(4-chloro-3-fluoro-phenyl)-1-2-(pyrrolidin-1-yl-ethyl)-1H-imidazol-2-yl]-piperidin-1-yl}-pyrimidin-4-ylamine;

5-cyclobutyl-6-{4-(3-trifluoromethyl-phenyl)-1-2-(pyrrolidin-1-yl-ethyl)-1H-imidazol-2-yl]-piperidin-1-yl}-pyrimidin-4-ylamine;

5-cyclobutyl-6-{4-(3-chloro-4-fluoro-phenyl)-1-2-(pyrrolidin-1-yl-ethyl)-1H-imidazol-2-yl]-piperidin-1-yl}-pyrimidin-4-ylamine;

5-cyclobutyl-6-{4-(4-chloro-phenyl)-1-2-(pyrrolidin-1-yl-ethyl)-1H-imidazol-2-yl]-piperidin-1-yl}-pyrimidin-4-ylamine;

5-cyclobutyl-6-{4-(3-chloro-phenyl)-1-2-(pyrrolidin-1-yl-ethyl)-1H-imidazol-2-yl]-piperidin-1-yl}-pyrimidin-4-ylamine;

5-Bromo-6-{4-(4-trifluoromethyl-phenyl)-1-2-pyrrolidin-1-yl-ethyl)-1H-imidazol-2-yl]-piperidin-1-yl}-pyrimidin-4-ylamine;

5-Bromo-6-{4-(4-chloro-3-fluorophenyl)-1-2-pyrrolidin-1-yl-ethyl)-1H-imidazol-2-yl]-piperidin-1-yl}-pyrimidin-4-ylamine;

5-Bromo-6-{4-(3-trifluoromethyl-phenyl)-1-2-pyrrolidin-1-yl-ethyl)-1H-imidazol-2-yl]-piperidin-1-yl}-pyrimidin-4-ylamine;

5-Bromo-6-{4-(3-chloro-4-fluorophenyl)-1-2-pyrrolidin-1-yl-ethyl)-1H-imidazol-2-yl]-piperidin-1-yl}-pyrimidin-4-ylamine;

5-vinyl-6-{4-(4-trifluoromethyl-phenyl)-1-2-(pyrrolidin-1-yl-ethyl)-1H-imidazol-2-yl]-piperidin-1-yl}-pyrimidin-4-ylamine;

6-{4-(4-trifluoromethyl-phenyl)-1-2-(pyrrolidin-1-yl-ethyl)-1H-imidazol-2-yl]-piperidin-1-yl}-pyrimidin-4-ylamine;

5-Ethyl-6-{4-(4-trifluoromethyl-phenyl)-1-2-(pyrrolidin-1-yl-ethyl)-1H-imidazol-2-yl]-piperidin-1-yl}-pyrimidin-4-ylamine;

5-Ethyl-6-{4-(3-trifluoromethyl-phenyl)-1-2-(pyrrolidin-1-yl-ethyl)-1H-imidazol-2-yl]-piperidin-1-yl}-pyrimidin-4-ylamine;

5-Ethyl-6-{4-(4-chloro-phenyl)-1-2-(pyrrolidin-1-yl-ethyl)-1H-imidazol-2-yl]-piperidin-1-yl}-pyrimidin-4-ylamine;

5-Ethyl-6-{4-(3-chloro-phenyl)-1-2-(pyrrolidin-1-yl-ethyl)-1H-imidazol-2-yl]-piperidin-1-yl}-pyrimidin-4-ylamine;

5-Ethyl-6-{4-(4-fluoro-3-trifluoromethyl-phenyl)-1-2-((3,3-difluoro-pyrrolidin-1-yl)-ethyl)-1H-imidazol-2-yl]-piperidin-1-yl}-pyrimidin-4-ylamine;

5-Ethyl-6-{4-(4-fluoro-3-trifluoromethyl-phenyl)-1-2-((piperidin-1-yl)-ethyl)-1H-imidazol-2-yl]-piperidin-1-yl}-pyrimidin-4-ylamine;

5-Ethyl-6-{4-(3-trifluoromethyl-phenyl)-1-2-(azetidin-1-yl-ethyl)-1H-imidazol-2-yl]-piperidin-1-yl}-pyrimidin-4-ylamine;

5-Ethyl-6-{4-(3-fluoro-phenyl)-1-2-(azetidin-1-yl-ethyl)-1H-imidazol-2-yl]-piperidin-1-yl}-pyrimidin-4-ylamine;

5-Ethyl-6-{4-(3-chloro-phenyl)-1-2-(azetidin-1-yl-ethyl)-1H-imidazol-2-yl]-piperidin-1-yl}-pyrimidin-4-ylamine;

5-cyclobutyl-6-{4-(3-fluoro-4-trifluoromethylphenyl)-1-2-(azetidin-1-yl-ethyl)-1H-imidazol-2-yl]-piperidin-1-yl}-pyrimidin-4-ylamine;

5-Ethyl-6-{4-(4-fluoro-3-chlorophenyl)-1-2-(azetidin-1-yl-ethyl)-1H-imidazol-2-yl]-piperidin-1-yl}-pyrimidin-4-ylamine;

5-Ethyl-6-{4-(3,4-difluorophenyl)-1-2-(azetidin-1-yl-ethyl)-1H-imidazol-2-yl]-piperidin-1-yl}-pyrimidin-4-ylamine;

5-Nitro-6-{4-(4-fluoro-3-trifluomethyl-phenyl)-1-2-(azetidin-1-yl-ethyl)-1H-imidazol-2-yl]-piperidin-1-yl}-pyrimidin-4-ylamine;

5-Amino-6-{4-(4-fluoro-3-trifluomethyl-phenyl)-1-2-(azetidin-1-yl-ethyl)-1H-imidazol-2-yl]-piperidin-1-yl}-pyrimidin-4-ylamine;

5-Formyl-6-{4-(4-fluoro-3-trifluomethyl-phenyl)-1-2-(azetidin-1-yl-ethyl)-1H-imidazol-2-yl]-piperidin-1-yl}-pyrimidin-4-ylamine;

6-{4-(4-fluoro-3-trifluomethyl-phenyl)-1-2-(pyrrolidin-1-yl-ethyl)-1H-imidazol-2-yl]-piperidin-1-yl}-pyrimidin-4-ylamine-5-carboxy acid;

5-Formyl-6-{4-(4-fluoro-3-trifluomethyl-phenyl)-1-2-(pyrrolidin-1-yl-ethyl)-1H-imidazol-2-yl]-piperidin-1-yl}-pyrimidin-4-ylamine;

5-Ethylamide-6-{4-(4-fluoro-3-trifluomethyl-phenyl)-1-2-(azetidin-1-yl-ethyl)-1H-imidazol-2-yl]-piperidin-1-yl}-pyrimidin-4-ylamine;

5-Ethoxy-6-{4-(3-chloro-4-fluorophenyl)-1-2-(pyrrolidin-1-yl-ethyl)-1H-imidazol-2-yl]-piperidin-1-yl}-pyrimidin-4-ylamine;

5-isopropoxy-6-{4-(3-chloro-4-fluorophenyl)-1-2-(pyrrolidin-1-yl-ethyl)-1H-imidazol-2-yl]-piperidin-1-yl}-pyrimidin-4-ylamine;

5-Ethoxy-6-{4-(4-fluoro-3-trifluomethyl-phenyl)-1-2-(N,N-dimethylamino-1-yl-ethyl)-1H-imidazol-2-yl]-piperidin-1-yl}-pyrimidin-4-ylamine;

5-Isoprpoxy-6-{4-(4-fluoro-3-trifluomethyl-phenyl)-1-2-(N,N-dimethylamino-1-yl-ethyl)-1H-imidazol-2-yl]-piperidin-1-yl}-pyrimidin-4-ylamine;

5-Ethoxy-6-{4-(4-fluoro-3-methyl-phenyl)-1-2-(N,N-dimethylamino-1-yl-ethyl)-1H-imidazol-2-yl]-piperidin-1-yl}-pyrimidin-4-ylamine;

5-isopropoxy-6-{4-(4-fluoro-3-methyl-phenyl)-1-2-(N,N-dimethylamino-1-yl-ethyl)-1H-imidazol-2-yl]-piperidin-1-yl}-pyrimidin-4-ylamine;

5-Ethyl-6-{4-(4-fluoro-3-methyl-phenyl)-1-2-(N,N-dimethylamino-1-yl-ethyl)-1H-imidazol-2-yl]-piperidin-1-yl}-pyrimidin-4-ylamine;

5-Ethyl-6-{4-(4-fluoro-3-methyl-phenyl)-1-2-(N,N-diethylamino-1-yl-ethyl)-1H-imidazol-2-yl]-piperidin-1-yl}-pyrimidin-4-ylamine;

5-Ethyl-6-{4-(4-fluoro-3-methyl-phenyl)-1-2-(pyrrolidin-1-yl-ethyl)-1H-imidazol-2-yl]-piperidin-1-yl}-pyrimidin-4-ylamine;

5-Ethoxy-6-{4-(4-fluoro-3-methyl-phenyl)-1-2-(pyrrolidin-1-yl-ethyl)-1H-imidazol-2-yl]-piperidin-1-yl}-pyrimidin-4-ylamine;

5-Isopropoxy-6-{4-(4-fluoro-3-methyl-phenyl)-1-2-(pyrrolidin-1-yl-ethyl)-1H-imidazol-2-yl]-piperidin-1-yl}-pyrimidin-4-ylamine;

5-Ethyl-6-{4-(4-fluoro-3-methyl-phenyl)-1-2-(N,N-isopropylethylamino-1-yl-ethyl)-1H-imidazol-2-yl]-piperidin-1-yl}-pyrimidin-4-ylamine;

5-Ethoxy-6-{4-(4-fluoro-3-methyl-phenyl)-1-2-(N,N-isopropylethylamino-1-yl-ethyl)-1H -imidazol-2-yl]-piperidin-1-yl}-pyrimidin-4-ylamine;

5-Isopropoxy-6-{4-(4-fluoro-3-methyl-phenyl)-1-2-(N,N-isopropylethylamino-1-yl-ethyl)-1H -imidazol-2-yl]-piperidin-1-yl}-pyrimidin-4-ylamine;

5-Ethoxy-6-{4-(4-fluoro-3-methyl-phenyl)-1-2-(N,N-diethylamino-1-yl-ethyl)-1H-imidazol-2-yl]-piperidin-1-yl}-pyrimidin-4-ylamine;

5-Isopropoxy-6-{4-(4-fluoro-3-methyl-phenyl)-1-2-(N,N-diethylamino-1-yl-ethyl)-1H-imidazol-2-yl]-piperidin-1-yl}-pyrimidin-4-ylamine;

4-amino-6-{4-(4-fluoro-3-trifluoromethyl-phenyl)-1-2-(pyrrolidin-1-yl-ethyl)-1H-imidazol-2-yl]-piperidin-1-yl}-pyrimidin-5-carbonitrile;

4-amino-6-{4-(3,4-difluorophenyl)-1-2-(pyrrolidin-1-yl-ethyl)-1H-imidazol-2-yl]-piperidin-1-yl}-pyrimidin-5-carbonitrile;

4-amino-6-{4-(3-chloro-4-fluorophenyl)-1-2-(pyrrolidin-1-yl-ethyl)-1H-imidazol-2-yl]-piperidin-1-yl}-pyrimidin-5-carbonitrile;

4-amino-6-{4-(4-fluorophenyl)-1-2-(pyrrolidin-1-yl-ethyl)-1H-imidazol-2-yl]-piperidin-1-yl}-pyrimidin-5-carbonitrile;

4-amino-6-{4-(3-fluorophenyl)-1-2-(pyrrolidin-1-yl-ethyl)-1H-imidazol-2-yl]-piperidin-1-yl}-pyrimidin-5-carbonitrile;

4-amino-6-{4-(3-trifluoromethyl-phenyl)-1-2-(pyrrolidin-1-yl-ethyl)-1H-imidazol-2-yl]-piperidin-1-yl}-pyrimidin-5-carbonitrile;

4-amino-6-{4-(3-chloro-phenyl)-1-2-(pyrrolidin-1-yl-ethyl)-1H-imidazol-2-yl]-piperidin-1-yl}-pyrimidin-5-carbonitrile;

4-amino-6-{4-(4-fluoro-3-trifluoromethyl-phenyl)-1-2-(piperidin-1-yl-ethyl)-1H-imidazol-2-yl]-piperidin-1-yl}-pyrimidin-5-carbonitrile;

4-amino-6-{4-(3,4-difluorophenyl)-1-2-(azetidin-1-yl-ethyl)-1H-imidazol-2-yl]-piperidin-1-yl}-pyrimidin-5-carbonitrile;

4-amino-6-{4-(4-fluoro-3-difluoromethoxy-phenyl)-1-2-(azetidin-1-yl-ethyl)-1H-imidazol-2-yl]-piperidin-1-yl}-pyrimidin-5-carbonitrile;

4-amino-6-{4-(2-oxo-1,2-dihydro-pyridin-4-yl)-1-2-(azetidin-1-yl-ethyl)-1H-imidazol-2-yl]-piperidin-1-yl}-pyrimidin-5-carbonitrile;

4-amino-6-{4-(4-methyl-3-trifluoromethyl-phenyl)-1-2-(azetidin-1-yl-ethyl)-1H-imidazol-2-yl]-piperidin-1-yl}-pyrimidin-5-carbonitrile;

4-amino-6-{4-(2-isopropyl-pyridin-4-yl)-1-2-(azetidin-1-yl-ethyl)-1H-imidazol-2-yl]-piperidin-1-yl}-pyrimidin-5-carbonitrile;

4-amino-6-{4-(2-ethyl-pyridin-4-yl)-1-2-(azetidin-1-yl-ethyl)-1H-imidazol-2-yl]-piperidin-1-yl}-pyrimidin-5-carbonitrile;

4-amino-6-{4-(2-cyclopropyl-pyridin-4-yl)-1-2-(azetidin-1-yl-ethyl)-1H-imidazol-2-yl]-piperidin-1-yl}-pyrimidin-5-carbonitrile;

4-amino-6-{4-(4-methyl-3-fluoro-phenyl)-1-2-(azetidin-1-yl-ethyl)-1H-imidazol-2-yl]-piperidin-1-yl}-pyrimidin-5-carbonitrile;

4-amino-6-{4-(4-methoxy-3-fluoro-phenyl)-1-2-(azetidin-1-yl-ethyl)-1H-imidazol-2-yl]-piperidin-1-yl}-pyrimidin-5-carbonitrile;

4-amino-6-{4-(4-methyl-3-chloro-phenyl)-1-2-(azetidin-1-yl-ethyl)-1H-imidazol-2-yl]-piperidin-1-yl}-pyrimidin-5-carbonitrile;

4-amino-6-{4-(4-methoxy-3-chloro-phenyl)-1-2-(azetidin-1-yl-ethyl)-1H-imidazol-2-yl]-piperidin-1-yl}-pyrimidin-5-carbonitrile;

4-amino-6-{4-(3-methyl-4-fluoro-phenyl)-1-2-(pyrrolidin-1-yl-ethyl)-1H-imidazol-2-yl]-piperidin-1-yl}-pyrimidin-5-carbonitrile;

4-amino-6-{4-(3-methyl-4-fluoro-phenyl)-1-2-(N,N-dimethylamino)-1-yl-ethyl)-1H-imidazol-2-yl]-piperidin-1-yl}-pyrimidin-5-carbonitrile;

4-amino-6-{4-(3-methyl-4-fluoro-phenyl)-1-2-(N,N-diethylamino)-1-yl-ethyl)-1H-imidazol-2-yl]-piperidin-1-yl}-pyrimidin-5-carbonitrile;

4-amino-6-{4-(3-methyl-4-fluoro-phenyl)-1-2-(N,N-isopropylethylamino)-1-yl-ethyl)-1H -imidazol-2-yl]-piperidin-1-yl}-pyrimidin-5-carbonitrile;

4-amino-6-{4-(3,4-difluorophenyl)-1-2-(azetidin-1-yl-ethyl)-1H-imidazol-2-yl]-piperidin-1-yl}-pyrimidin-5-carboxylic acid amide;

4-amino-6-{4-(3,4-difluorophenyl)-1-2-(pyrrolidin-1-yl-ethyl)-1H-imidazol-2-yl]-piperidin-1-yl}-pyrimidin-5-carboxylic acid amide;

4-amino-6-{4-(3-chloro-4-fluorophenyl)-1-2-(pyrrolidin-1-yl-ethyl)-1H-imidazol-2-yl]-piperidin-1-yl}-pyrimidin-5-carboxylic acid amide;

4-amino-6-{4-(4-fluoro-3-trifluoromethylphenyl)-1-2-(pyrrolidin-1-yl-ethyl)-1H-imidazol-2-yl]-piperidin-1-yl}-pyrimidin-5-carboxylic acid amide;

4-amino-6-{4-(2-isopropyl-pyridin-4-yl)-1-2-(azetidin-1-yl-ethyl)-1H-imidazol-2-yl]-piperidin-1-yl}-pyrimidin-5-carboxylic acid amide;

4-amino-6-{4-(4-fluorophenyl)-1-2-(pyrrolidin-1-yl-ethyl)-1H-imidazol-2-yl]-piperidin-1-yl}-pyrimidin-5-carboxylic acid amide;

4-amino-6-{4-(3-fluorophenyl)-1-2-(pyrrolidin-1-yl-ethyl)-1H-imidazol-2-yl]-piperidin-1-yl}-pyrimidin-5-carboxylic acid amide;

4-amino-6-{4-(3-trifluoromethyl-phenyl)-1-2-(pyrrolidin-1-yl-ethyl)-1H-imidazol-2-yl]-piperidin-1-yl}-pyrimidin-5-carboxylic acid amide;

4-amino-6-{4-(3-chloro-phenyl)-1-2-(pyrrolidin-1-yl-ethyl)-1H-imidazol-2-yl]-piperidin-1-yl}-pyrimidin-5-carboxylic acid amide;

4-amino-6-{4-(4-fluoro-3-trifluoromethyl-phenyl)-1-2-(piperidin-1-yl-ethyl)-1H-imidazol-2-yl]-piperidin-1-yl}-pyrimidin-5-carboxylic acid amide;

4-amino-6{4-(4-fluoro-3-difluoromethoxy-phenyl)-1-2-(azetidin-1-yl-ethyl)-1H-imidazol-2-yl]-piperidin-1-yl}-pyrimidin-5-carboxylic acid amide;

4-amino-6-{4-(2-oxo-pyridin-4-yl)-1-2-(azetidin-1-yl-ethyl)-1H-imidazol-2-yl]-piperidin-1-yl}-pyrimidin-5-carboxylic acid amide;

4-amino-6-{4-(4-methyl-3-trifluomethyl-phenyl)-1-2-(azetidin-1-yl-ethyl)-1H-imidazol-2-yl]-piperidin-1-yl}-pyrimidin-5-carboxylic acid amide;

4-amino-6-{4-(2-ethyl-pyridin-4-yl)-1-2-(azetidin-1-yl-ethyl)-1H-imidazol-2-yl]-piperidin-1-yl}-pyrimidin-5-carboxylic acid amide;

4-amino-6-{4-(2-cylopropyl-pyridin-4-yl)-1-2-(azetidin-1-yl-ethyl)-1H-imidazol-2-yl]-piperidin-1-yl}-pyrimidin-5-carboxylic acid amide;

4-amino-6-{4-(2-tert-butyl-pyridin-4-yl)-1-2-(azetidin-1-yl-ethyl)-1H-imidazol-2-yl]-piperidin-1-yl}-pyrimidin-5-carboxylic acid amide;

4-amino-6-{4-(4-methyl-3-fluoro-phenyl)-1-2-(azetidin-1-yl-ethyl)-1H-imidazol-2-yl]-piperidin-1-yl}-pyrimidin-5-carboxylic acid amide;
4-amino-6-{4-(4-methoxy-3-fluoro-phenyl)-1-2-(azetidin-1-yl-ethyl)-1H-imidazol-2-yl]-piperidin-1-yl}-pyrimidin-5-carboxylic acid amide;
4-amino-6-{4-(3-chloro-4-methyl-phenyl)-1-2-(azetidin-1-yl-ethyl)-1H-imidazol-2-yl]-piperidin-1-yl}-pyrimidin-5-carboxylic acid amide;
4-amino-6-{4-(3-chloro-4-methoxy-phenyl)-1-2-(azetidin-1-yl-ethyl)-1H-imidazol-2-yl]-piperidin-1-yl}-pyrimidin-5-carboxylic acid amide;
4-amino-6-{4-(4-fluoro-3-methyl-phenyl)-1-2-(N,N-dimethylamino-ethyl)-1H-imidazol-2-yl]-piperidin-1-yl}-pyrimidin-5-carboxylic acid amide;
4-amino-6-{4-(4-fluoro-3-methyl-phenyl)-1-2-(N,N-diethylamino-ethyl)-1H-imidazol-2-yl]-piperidin-1-yl}-pyrimidin-5-carboxylic acid amide;
4-amino-6-{4-(4-fluoro-3-methyl-phenyl)-1-2-(pyrrolidin-1-yl-ethyl)-1H-imidazol-2-yl]-piperidin-1-yl}-pyrimidin-5-carboxylic acid amide;
4-amino-6-{4-(4-fluoro-3-methyl-phenyl)-1-2-(N,N-ethyl-isopropylamino-ethyl)-1H-imidazol-2-yl]-piperidin-1-yl}-pyrimidin-5-carboxylic acid amide;
6-{4-[1-(2-Azetidin-1-yl-ethyl)-4-(2-dimethylamino-pyrimidin-5-yl)-1H-imidazol-2-yl]-piperidin-1-yl}-5-ethyl-pyrimidin-4-ylamine;
4-Amino-6-{4-[1-(2-azetidin-1-yl-ethyl)-4-(2-fluoro-phenyl)-1H-imidazol-2-yl]-piperidin-1-yl}-pyrimidine-5-carbonitrile;
3-[2-[1-(6-Amino-5-cyano-pyrimidin-4-yl)-piperidin-4-yl]-1-(2-azetidin-1-yl-ethyl)-1H-imidazol-4-yl]-benzenesulfonamide;
4-Amino-6-{4-[1-(2-azetidin-1-yl-ethyl)-4-(3-methanesulfonyl-phenyl)-1H-imidazol-2-yl]-piperidin-1-yl}-pyrimidine-5-carbonitrile;
4-Amino-6-{4-[1-(2-azetidin-1-yl-ethyl)-4-(3-methanesulfonyl-phenyl)-1H-imidazol-2-yl]-piperidin-1-yl}-pyrimidine-5-carboxylic acid amide;
4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carbonitrile;
4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carbonitrile;
4-Amino-6-{4-[1-[2-(cyclopropylmethyl-amino)-ethyl]-4-(4-fluoro-3-trifluoromethyl-phenyl)-1H-imidazol-2-yl]-piperidin-1-yl}-pyrimidine-5-carboxylic acid amide;
4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carbonitrile;
4-Amino-6-(4-{4-(4-fluoro-3-trifluoromethyl-phenyl)-1-[2-(isopropyl-methyl-amino)-ethyl]-1H-imidazol-2-yl}-piperidin-1-yl)-pyrimidine-5-carboxylic acid amide;
4-Amino-6-{4-[1-{2-[(2-dimethylamino-ethyl)-methyl-amino]-ethyl}-4-(4-fluoro-3-trifluoromethyl-phenyl)-1H-imidazol-2-yl]-piperidin-1-yl}-pyrimidine-5-carbonitrile;
4-Amino-6-[4-(4-(4-fluoro-3-trifluoromethyl-phenyl)-1-{2-[(2-methoxy-ethyl)-methyl-amino]-ethyl}-1H-imidazol-2-yl)-piperidin-1-yl]-pyrimidine-5-carbonitrile;
4-Amino-6-(4-{4-(4-fluoro-3-trifluoromethyl-phenyl)-1-[2-(2-methoxy-ethylamino)-ethyl]-1H-imidazol-2-yl}-piperidin-1-yl)-pyrimidine-5-carbonitrile;
4-Amino-6-{4-[1-{2-[(2-dimethylamino-ethyl)-methyl-amino]-ethyl}-4-(4-fluoro-3-trifluoromethyl-phenyl)-1H-imidazol-2-yl]-piperidin-1-yl}-pyrimidine-5-carboxylic acid amide;
4-Amino-6-[4-(4-(4-fluoro-3-trifluoromethyl-phenyl)-1-{2-[(2-methoxy-ethyl)-methyl-amino]-ethyl}-1H-imidazol-2-yl)-piperidin-1-yl]-pyrimidine-5-carboxylic acid amide;
4-Amino-6-(4-{4-(4-fluoro-3-trifluoromethyl-phenyl)-1-[2-(2-methoxy-ethylamino)-ethyl]-1H-imidazol-2-yl}-piperidin-1-yl)-pyrimidine-5-carboxylic acid amide;
4-Amino-6-{4-[1-[2-(benzyl-methyl-amino)-ethyl]-4-(4-fluoro-3-trifluoromethyl-phenyl)-1H-imidazol-2-yl]-piperidin-1-yl}-pyrimidine-5-carboxylic acid amide;
4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5-carbonitrile;
4-Amino-6-{4-[4-(4-fluoro-3-trifluoromethyl-phenyl)-1-(2-isopropylamino-ethyl)-1H-imidazol-2-yl]-piperidin-1-yl}-pyrimidine-5-carboxylic acid amide;
4-Amino-6-(4-{4-(4-fluoro-3-trifluoromethyl-phenyl)-1-[2-(2-methoxy-1-methyl-ethylamino)-ethyl]-1H-imidazol-2-yl}-piperidin-1-yl)-pyrimidine-5-carboxylic acid amide;
4-Amino-6-{4-[4-(4-fluoro-3-trifluoromethyl-phenyl)-1-(2-isobutylamino-ethyl)-1H-imidazol-2-yl]-piperidin-1-yl}-pyrimidine-5-carbonitrile;
4-Amino-6-{4-[4-(4-fluoro-3-trifluoromethyl-phenyl)-1-(2-isobutylamino-ethyl)-1H-imidazol-2-yl]-piperidin-1-yl}-pyrimidine-5-carboxylic acid amide;
4-Amino-6-{4-[4-(4-fluoro-3-trifluoromethyl-phenyl)-1-(2-methylamino-ethyl)-1H-imidazol-2-yl]-piperidin-1-yl}-pyrimidine-5-carbonitrile;
4-Amino-6-{4-[1-(2-tert-butylamino-ethyl)-4-(4-fluoro-3-trifluoromethyl-phenyl)-1H-imidazol-2-yl]-piperidin-1-yl}-pyrimidine-5-carbonitrile;
4-Amino-6-{4-[4-(4-fluoro-3-trifluoromethyl-phenyl)-1-(2-methylamino-ethyl)-1H-imidazol-2-yl]-piperidin-1-yl}-pyrimidine-5-carboxylic acid amide;
4-Amino-6-{4-[1-(2-tert-butylamino-ethyl)-4-(4-fluoro-3-trifluoromethyl-phenyl)-1H-imidazol-2-yl]-piperidin-1-yl}-pyrimidine-5-carboxylic acid amide;
4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carbonitrile;
4-Amino-6-(4-{4-(4-fluoro-3-methyl-phenyl)-1-[2-(isopropyl-methyl-amino)-ethyl]-1H-imidazol-2-yl}-piperidin-1-yl)-pyrimidine-5-carbonitrile;
4-Amino-6-{4-[4-(4-fluoro-3-methyl-phenyl)-1-(2-isopropylamino-ethyl)-1H-imidazol-2-yl]-piperidin-1-yl}-pyrimidine-5-carbonitrile;
4-Amino-6-{4-[1-(2-cyclopentylamino-ethyl)-4-(4-fluoro-3-trifluoromethyl-phenyl)-1H-imidazol-2-yl]-piperidin-1-yl}-pyrimidine-5-carbonitrile;
4-Amino-6-{4-[1-[2-(1,1-dimethyl-propylamino)-ethyl]-4-(4-fluoro-3-trifluoromethyl-phenyl)-1H-imidazol-2-yl]-piperidin-1-yl}-pyrimidine-5-carbonitrile;
4-Amino-6-{4-[1-[2-(cyclopropylmethyl-amino)-ethyl]-4-(4-fluoro-3-methyl-phenyl)-1H-imidazol-2-yl]-piperidin-1-yl}-pyrimidine-5-carboxylic acid amide;
4-Amino-6-{4-[4-(4-fluoro-3-methyl-phenyl)-1-(2-hydroxy-ethyl)-1H-imidazol-2-yl]-piperidin-1-yl}-pyrimidine-5-carbonitrile;
4-Amino-6-(4-{4-(4-fluoro-3-methyl-phenyl)-1-[2-(isopropyl-methyl-amino)-ethyl]-1H-imidazol-2-yl}-piperidin-1-yl)-pyrimidine-5-carboxylic acid amide;
4-Amino-6-{4-[4-(4-fluoro-3-methyl-phenyl)-1-(2-isopropylamino-ethyl)-1H-imidazol-2-yl]-piperidin-1-yl}-pyrimidine-5-carboxylic acid amide;
4-Amino-6-{4-[1-(2-cyclopentylamino-ethyl)-4-(4-fluoro-3-trifluoromethyl-phenyl)-1H-imidazol-2-yl]-piperidin-1-yl}-pyrimidine-5-carboxylic acid amide;

4-Amino-6-{4-[1-[2-(1,1-dimethyl-propylamino)-ethyl]-4-(4-fluoro-3-trifluoromethyl-phenyl)-1H-imidazol-2-yl]-piperidin-1-yl}-pyrimidine-5-carboxylic acid amide;
4-Amino-6-{4-[1-(2-cyclopentylamino-ethyl)-4-(4-fluoro-3-methyl-phenyl)-1H-imidazol-2-yl]-piperidin-1-yl}-pyrimidine-5-carbonitrile;
4-Amino-6-{4-[4-(4-fluoro-3-methyl-phenyl)-1-(2-isobutylamino-ethyl)-1H-imidazol-2-yl]-piperidin-1-yl}-pyrimidine-5-carbonitrile;
4-Amino-6-{4-[1-(2-cyclopentylamino-ethyl)-4-(4-fluoro-3-methyl-phenyl)-1H-imidazol-2-yl]-piperidin-1-yl}-pyrimidine-5-carboxylic acid amide;
4-Amino-6-{4-[4-(4-fluoro-3-methyl-phenyl)-1-(2-isobutylamino-ethyl)-1H-imidazol-2-yl]-piperidin-1-yl}-pyrimidine-5-carboxylic acid amide;
4-Amino-6-{4-[4-(4-fluoro-3-methyl-phenyl)-1-(2-hydroxy-ethyl)-1H-imidazol-2-yl]-piperidin-1-yl}-pyrimidine-5-carboxylic acid amide;
4-Amino-6-{4-[4-(4-fluoro-3-methyl-phenyl)-1-(2-methylamino-ethyl)-1H-imidazol-2-yl]-piperidin-1-yl}-pyrimidine-5-carbonitrile;
4-Amino-6-{4-[4-(4-fluoro-3-trifluoromethyl-phenyl)-1-(2-hydroxy-ethyl)-1H-imidazol-2-yl]-piperidin-1-yl}-pyrimidine-5-carboxylic acid amide;
2-[2-[1-(6-Amino-5-ethoxy-pyrimidin-4-yl)-piperidin-4-yl]-4-(4-fluoro-3-methyl-phenyl)-imidazol-1-yl]-ethanol;
4-Amino-6-{4-[4-(4-fluoro-3-methyl-phenyl)-1-(2-methylamino-ethyl)-1H-imidazol-2-yl]-piperidin-1-yl}-pyrimidine-5-carboxylic acid amide;
5-Ethoxy-6-{4-[4-(4-fluoro-3-trifluoromethyl-phenyl)-1-(2-isopropylamino-ethyl)-1H-imidazol-2-yl]-piperidin-1-yl}-pyrimidin-4-ylamine;
{3-[2-[1-(6-Amino-5-isopropyl-pyrimidin-4-yl)-piperidin-4-yl]-4-(4-fluoro-3-methyl-phenyl)-imidazol-1-ylmethyl]-azetidin-1-yl}-methanol; and
5-Ethyl-6-{4-[4-(4-fluoro-3-methyl-phenyl)-1-(1-methyl-azetidin-3-ylmethyl)-1H-imidazol-2-yl]-piperidin-1-yl}-pyrimidin-4-ylamine.

In certain embodiments, $R^1$ is Hal, LA, O(LA), CN, $CONH_2$, CHO, or a $C_{5-10}$ aryl or $C_{6-15}$ fused aryl, a 3-12 membered saturated or partially unsaturated monocyclic or bicycic carbocyclic ring, a 3-12 membered monocyclic or bicyclic heterocylic ring having 1-4 heteroatoms independently selected from nitrogen, oxygen, or sulfur, or a 5-12 membered monocyclic or bicyclic heteroaryl ring having 1-4 heteroatoms independently selected from nitrogen, oxygen, or sulfur; each of which is optionally mono-, di- or trisubstituted by Hal, LA, OH, O(LA), $NH_2$ and/or NH(LA), $N(LA)_2$, $NO_2$, CN, OCN, SCN, COOH, COO(LA), $CONH_2$, CONH(LA), $CON(LA)_2$, NHCO(LA), NHCONH(LA), $NHCONH_2$, $NHSO_2(LA)$, CHO, CO(LA), $SO_2NH_2$, $SO_2(LA)$ and/or $SO_2H$, or an unbranched or branched linear or cyclic alkyl having 1, 2, 3, 4, 5, 6, 7 or 8 C atoms, in which one or two $CH_2$ groups may be replaced by an O atom and/or by an —NH—, NH(LA), —CO—, —NHCO— or —CH=CH— group, and/or in which a CH group may be replaced by —N—.

In certain embodiments, $R^1$ is Cl or Br. In certain embodiments, $R^1$ is CN, $CONH_2$, or CHO.

In certain embodiments, $R^1$ is methyl, ethyl, n-propyl, i-propyl, n-pentyl, i-pentyl, n-pentyl, straight chain or branched hexyl, or straight chain or branched pentyl, each of which is optionally substituted. In certain embodiments, $R^1$ is ethyl or i-propyl.

In certain embodiments, $R^1$ is O(LA).

In certain embodiments, $R^1$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]biclclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^1$ is an optionally substituted cyclopropyl, cyclobutyl, cyclopentyl, cyclohexyl, cycloheptyl, or cyclooctyl. In certain embodiments, $R^1$ is an optionally substituted cyclopropyl or cyclobutyl.

In certain embodiments, $R^1$ is an optionally substituted phenyl, pyridinyl, or pyrazolyl.

In certain embodiments the substituents designated $R^1$ are provided in Table 1.

TABLE 1

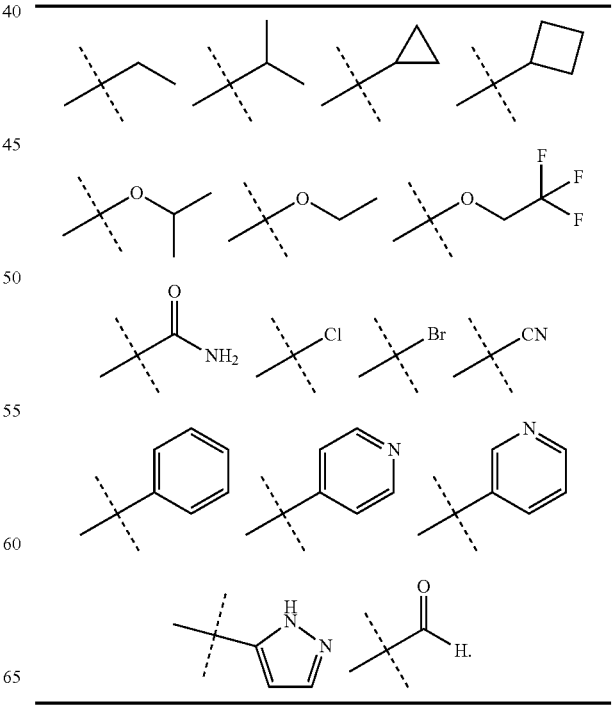

In certain embodiments, R³ is an unbranched or branched linear or mono- or bicyclic alkyl group having 1, 2, 3, 4, 5, 6, 7, 8 or 9 C atoms, in which one or two CH₂ groups may be replaced by an —O— or —NH— group, and/or in which one or two CH groups may be replaced by —N—, and/or in which 1, 2 or 3 H atoms may be replaced by Hal or OH.

In certain embodiments the substituents designated R³ are provided in Table 2.

TABLE 2

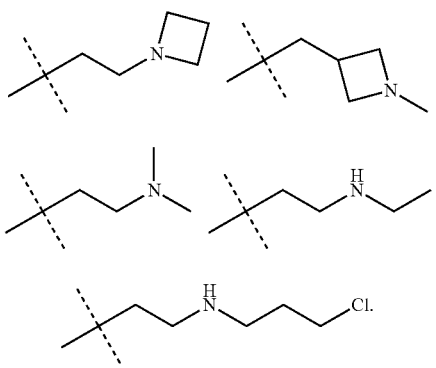

In certain embodiments, R² is $C_{5-10}$ aryl or a 5-12 membered monocyclic heteroaryl ring having 1-4 heteroatoms independently selected from nitrogen, oxygen, or sulfur; each of which is optionally mono-, di- or trisubstituted by Hal, LA, OH, O(LA), NH₂ and/or NH(LA), N(LA)₂, NO₂, CN, OCN, SCN, COOH, COO(LA), CONH₂, CONH(LA), CON(LA)₂, NHCO(LA), NHCONH(LA), NHCONH₂, NHSO₂(LA), CHO, CO(LA), SO₂NH₂, SO₂(LA).

In certain embodiments, R² is phenyl, furanyl, furazanyl, imidazolidinyl, imidazolinyl, imidazolyl, isothiazolyl, isoxazolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, thiophenyl, triazinyl, 1,2,3-triazolyl, 1,2,4-triazolyl, 1,2,5-triazolyl, or 1,3,4-triazolyl; each of which is optionally substituted. In certain embodiments, R² is an optionally substituted phenyl or pyridinyl.

In certain embodiments the substituents designated R² are provided in Table 3.

TABLE 3

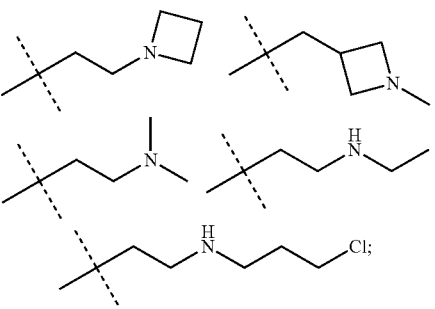

TABLE 3-continued

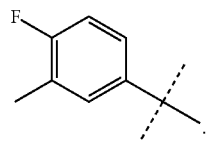

In certain embodiments, the invention provides a compound of formula I, wherein

R¹ is selected from

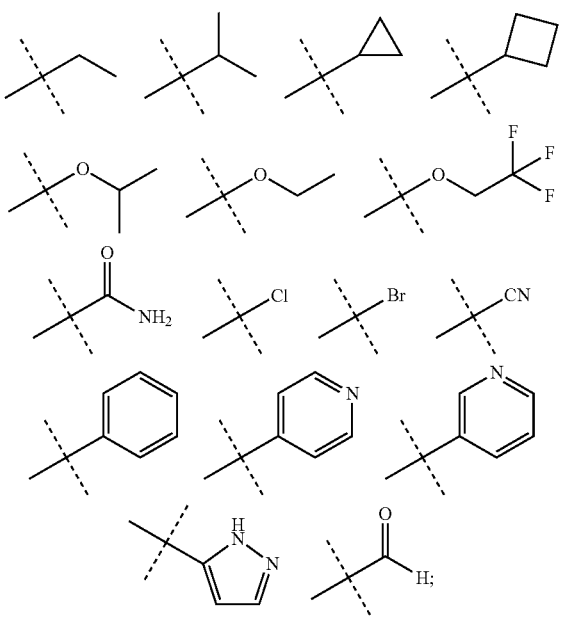

R³ is selected from

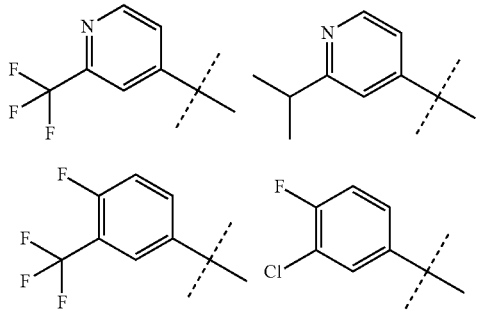

and

R² is selected from

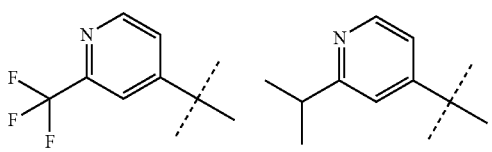

-continued

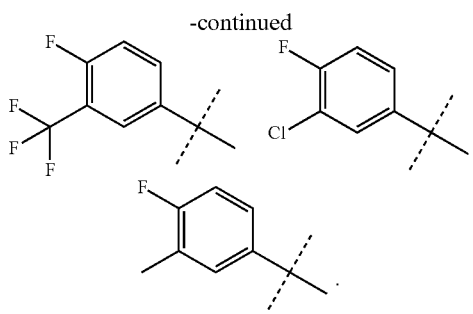

In certain embodiments, the invention provides a compound of formula I, wherein
- $R^1$ is methyl, ethyl, n-propyl, i-propyl, n-pentyl, i-pentyl, n-pentyl, straight chain or branched hexyl, or straight chain or branched pentyl, each of which is optionally substituted;
- $R^3$ is an unbranched or branched linear or mono- or bicyclic alkyl group having 1, 2, 3, 4, 5, 6, 7, 8 or 9 C atoms, in which one or two $CH_2$ groups may be replaced by an —O—, —NH—, group, and/or in which one or two CH groups may be replaced by —N—, and/or in which 1, 2 or 3 H atoms may be replaced by Hal or OH; and
- $R^2$ is phenyl, furanyl, furazanyl, imidazolidinyl, imidazolinyl, imidazolyl, isothiazolyl, isoxazolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, thiophenyl, triazinyl, 1,2,3-triazolyl, 1,2,4-triazolyl, 1,2,5-triazolyl, or 1,3,4-triazolyl; each of which is optionally substituted.

In certain embodiments, the invention provides a compound of formula I, wherein
- $R^1$ is ethyl or i-propyl;
- $R^3$ is an unbranched or branched linear or mono- or bicyclic alkyl group having 1, 2, 3, 4, 5, 6, 7, 8 or 9 C atoms, in which one or two $CH_2$ groups may be replaced by an —O—, —NH—, group, and/or in which one or two CH groups may be replaced by —N—, and/or in which 1, 2 or 3 H atoms may be replaced by Hal or OH; and
- $R^2$ is phenyl or pyridinyl; each of which is optionally substituted.

In certain embodiments, the invention provides a compound of formula I, wherein
- $R^1$ is ethyl or i-propyl;
- $R^3$ is selected from

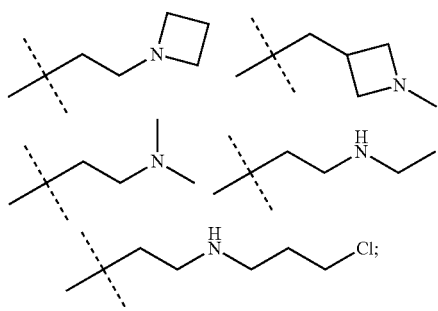

and
$R^2$ is selected from

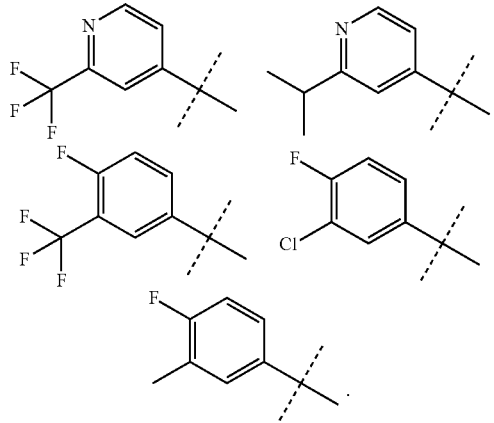

In certain embodiments, the invention provides a compound of formula I, wherein
- $R^1$ is ethyl or i-propyl;
- $R^3$ is

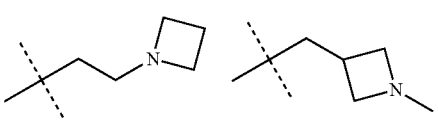

and
$R^2$ is selected from

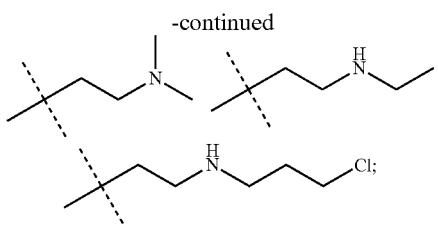

and
R² is

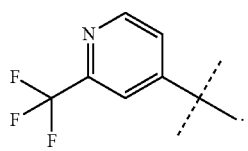

In certain embodiments, the invention provides a compound selected from any one of compounds 1 to 32 in the Examples provided below.

In certain embodiments, the invention provides compound 1. In certain embodiments, the invention provides compound 2. In certain embodiments, the invention provides compound 3. In certain embodiments, the invention provides compound 4. In certain embodiments, the invention provides compound 5. In certain embodiments, the invention provides compound 6. In certain embodiments, the invention provides compound 7. In certain embodiments, the invention provides compound 8. In certain embodiments, the invention provides compound 9. In certain embodiments, the invention provides compound 10. In certain embodiments, the invention provides compound 11. In certain embodiments, the invention provides compound 12. In certain embodiments, the invention provides compound 13. In certain embodiments, the invention provides compound 14. In certain embodiments, the invention provides compound 5. In certain embodiments, the invention provides compound 15. In certain embodiments, the invention provides compound 16. In certain embodiments, the invention provides compound 17. In certain embodiments, the invention provides compound 18. In certain embodiments, the invention provides compound 19. In certain embodiments, the invention provides compound 20. In certain embodiments, the invention provides compound 21. In certain embodiments, the invention provides compound 22. In certain embodiments, the invention provides compound 23. In certain embodiments, the invention provides compound 24. In certain embodiments, the invention provides compound 25. In certain embodiments, the invention provides compound 26. In certain embodiments, the invention provides compound 27. In certain embodiments, the invention provides compound 28. In certain embodiments, the invention provides compound 29. In certain embodiments, the invention provides compound 30. In certain embodiments, the invention provides compound 31. In certain embodiments, the invention provides compound 32.

In general, all residues which occur more than once may be identical or different, i.e. are independent of one another.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like. If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In cases where the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

All physiologically acceptable salts, derivatives, solvates, solvates of salts, and stereoisomers of these compounds, including mixtures thereof in all ratios, are also in accordance with the invention.

The compounds of Formula (I) may have one or more centers of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures.

Furthermore, the present invention relates to pharmaceutical compositions comprising a compound of the present invention, or a prodrug compound thereof, or a pharmaceutically acceptable salt or solvate thereof as an active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or a prodrug compound or other p70S6K inhibitors. The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In certain embodiments, the cancer to be treated is chosen from breast, colorectal, lung, prostate or pancreatic cancer or glioblastoma.

The invention also relates to the use of compounds according to the invention for the preparation of a medicament for the treatment of hyperproliferative diseases related to the hyperactivity of p70S6K as well as diseases modulated by the p70S6K cascade in mammals, or disorders mediated by aberrant proliferation, such as cancer and inflammation.

The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and sclerodema, diabetes, diabetic retinopathy, retinopathy of prematurity and age-related macular degeneration.

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of another anti-cancer therapeutic, wherein the amounts of the compound, salt, solvate, or prodrug, and of the chemotherapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, antimetabolites, intercalating antibiotics, growth factor inhibitors, cell cycle inhibitors, enzymes, topoisomerase inhibitors, biological response modifiers, anti-hormones, angiogenesis inhibitors, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of another protein kinase, auch as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinibl, XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[23]; celmoleukin, tasonermin, teceleukin, oprelvekin[1,3], recombinant interferon beta-1e;

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3] trebananib[2,3], virulizin[4], carfilzomib[1,3], endostatin[4], immucothel[4], belinostat[3], MGN-1703[4]. ([1]Prop. INN (Proposed International Nonproprietary Name); [2]Rec. INN (Recommended International Nonproprietary Names); [3]USAN (United States Adopted Name); [4] no INN).

This invention further relates to a method for inhibiting abnormal cell growth in a mammal or treating a hyperproliferative disorder that comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method for inhibiting abnormal cell growth in a mammal that comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed.

Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of animal body weight, preferably given as a single daily dose. For most large mammals, the total daily dosage is from about 0.2 milligrams to about 2000 milligrams, preferably from about 0.5 milligram to about 1000 milligrams. In the case of a 70 kg adult human, the total daily dose will generally be from about 0.5 milligrams to about 1000 milligrams. These aforementioned dosage regimens may be adjusted to provide the optimal therapeutic response.

The invention also relates to a set (kit) consisting of separate packs of
a) an effective amount of a compound according to the invention or a physiologically acceptable salt, solvate or prodrug thereof, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

EXPERIMENTAL SECTION

Some abbreviations that may appear in this application are as follows:

Abbreviations

| Designation | |
|---|---|
| ACN | acetonitrile |
| AcOH | Acetic acid |
| AIBN | Azobisisobutylonitrile |
| ATP | Adenosine triphosphate |
| b | Broad peak |
| Bop-Cl | Bis(2-oxo-3-oxazolidinyl)phosphinic chloride |
| Conc. | concentrated |
| d | Doublet |
| DCM | Dichloromethane |
| DCE | dichloroethane |
| DMAP | dimethylaminopyridine |
| DMF | dimethylformamide |
| DMSO | dimethylsulfoxide |
| DIEA/DIPEA | N,N-Diisopropylethylamine |
| DTT | dithiothreitol |
| EDTA | Ethylenediaminetetraacetic acid |
| equiv./eq. | equivalents |
| Et | ethyl |
| h/hr | hour |
| HEPES | 4-(2-hydroxyethyl)-1-piperazineethanesulfonic acid |
| HPLC | High pressure liquid chromatography |
| LC/MS | Liquid chromatography coupled to mass spectrometry |
| LiOH | Lithium hydroxide |
| m | multiplet |
| M | Molecular ion |
| m/z | Mass-to-charge ratio |
| Me | methyl |
| MeOH | methanol |
| min | minute |
| MS | Mass spectrometry |
| N | Normal (unit of concentration) |
| NaOH | Sodium hydroxide |
| NBS | N-bromosuccinimide |
| NMO | 4-methylmorpholine N-oxide |
| NMP | N-Methyl-2-pyrrolidone |
| NMR | Nuclear Magnetic Resonance |
| PG | Protecting group |
| psi | Pounds per square inch |
| PyBOP | (Benzotriazol-1-yloxy)tripyrrolidinophosphonium hexafluorophosphate |
| q | Quartette (or quartet) |
| Rf | Retention factor |
| RT/rt | Room temperature |
| Rt. | Retention time |
| s | Singlet |
| T3P | Propylphosphonic anhydride |
| TBAF | Tetrabutylammonium fluoride |
| Tert | Tertiary |
| TEA | Triethylamine |
| TFA | Trifluoroacetic acid |
| THAB | Tetrahexylammonium bromide |
| THF | Tetrahydrofuran |
| UV | ultraviolet |
| VIS | visible |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example. Unless otherwise indicated in the schemes, the variables have the same meaning as described above. Unless otherwise specified, all starting materials are obtained from commercially suppliers and used without further purifications. Unless otherwise specified, all temperatures are expressed in ° C. and all reactions are conducted at room temperature. Compounds were purified by either silica chromatography or preparative HPLC.

The present invention also relates to processes for manufacturing the compounds of the invention according to the hereinafter described schemes and working examples.

Generic Synthetic Scheme

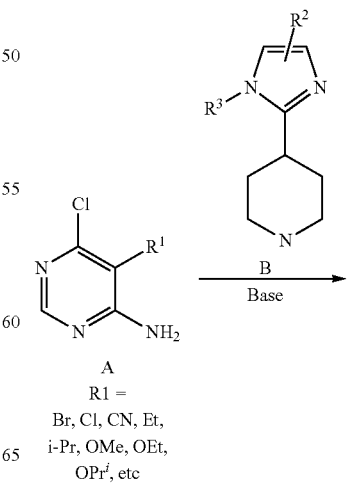

R1 = Br, Cl, CN, Et, i-Pr, OMe, OEt, OPr$^i$, etc

-continued

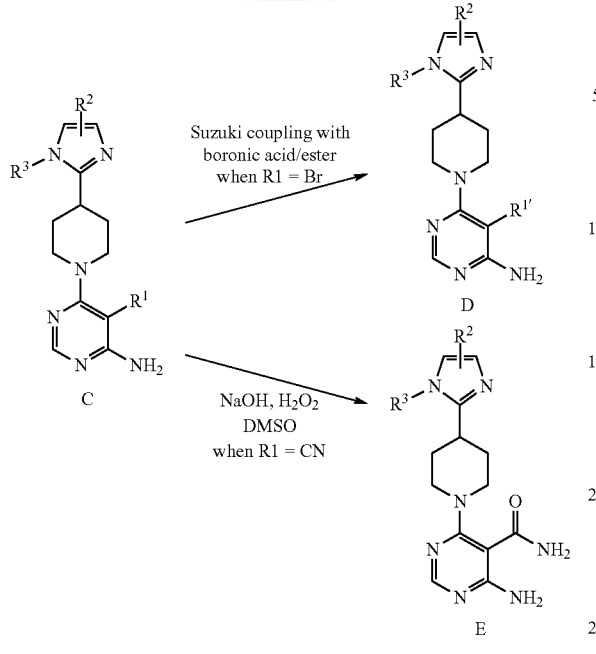

The aminopyrimidine chloride A (commercially available or prepared according to WO2013040059) was reacted with secondary amine B (prepared according to WO2013040059) in the presence of base to provide the desired compound C. A Suzuki coupling was then performed with compounds C while R1 is bromide to yield compound D. Hydrolysis of the compounds C while R1 is nitrile provided compounds E.

Analytical Methodology

Analytical LC/MS was performed using the following three methods:

Method A: A Discovery $C^{18}$, 5 μm, 3×30 mm column was used at a flow rate of 400 μL/min, sample loop 5 μL, mobile phase: (A) water with 0.1% formic acid, mobile phase, (B) methanol with 0.1% formic acid; retention times are given in minutes. Method details: (I) runs on a Quaternary Pump G1311A (Agilent) with UV/VIS diode array detector G1315B (Agilent) and Finnigan LCQ Duo MS detector in ESI+ modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry $C^{18}$, 3.5 μm, 4.6×75 mm column at a flow rate of 1 mL/min, sample loop 10 μL, mobile phase (A) is water with 0.05% TFA, mobile phase (B) is ACN with 0.05% TFA; retention times are given in minutes. Methods details: (I) runs on a Binary Pump G1312A (Agilent) with UV/Vis diode array detector G1315B (Agilent) and Agilent G1956B (SL) MS detector in ESI+ mode with UV-detection at 254 and 280 nm with a gradient of 20-85% (B) in a 10 min linear gradient (II) hold for 1 min at 85% (B) (III) decrease from 20-85% (B) in a 0.2 min linear gradient (IV) hold for 3.8 min at 20% (B).

Method C: Gradient: 4.2 min/Flow: 2 ml/min 99:01-0:100 Water+0.1%(Vol.) TFA; Acetonitril+0.1%(Vol.) TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Analytical Chiral HPLC

Analytical chiral HPLC was performed using a ChiralPak AD-H column (250×4.6 mm) from Daicel Chemical Industries, Ltd. on an Agilent 1100 Series system. The method used a 5.0 μL injection volume, with a flow rate of 1 mL/min of 100% methanol for 15 min at 25° C., and UV-detection at 254 and 280 nm.

Preparative HPLC

Preparative HPLC was performed using either a Waters Atlantis $dC_{18}$ OBD™ 10 μM (30×250 mm) column or a Waters Sunfire Prep $C_{18}$ OBD 10 μM (30×250 mm) column. The columns were used at a flow rate of 60 mL/min on a Waters Prep LC 4000 System equipped with a sample loop (10 mL) and an ISCO UA-6 UV/Vis detector. The mobile phase was drawn from two solvent reservoirs containing (A) water and (B) HPLC-grade acetonitrile. A typical preparative run used a linear gradient (e.g., 0-60% solvent B over 60 min).

EXAMPLE 1

Synthesis of Compounds

6-{4-[1-(2-Azetidin-1-yl-ethyl)-4-(4-fluoro-3-methyl-phenyl)-1H-imidazol-2-yl]-piperidin-1-yl}-5-ethyl-pyrimidin-4-ylamine (1)

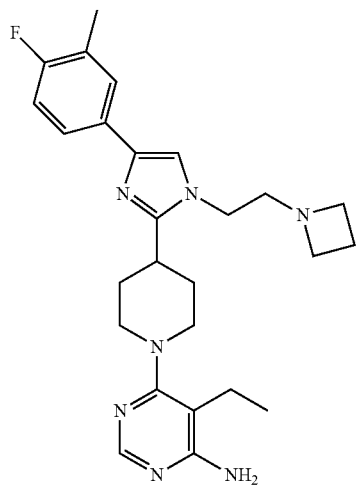 [SMILES: CCc1c(N)ncnc1N1CCC(c2nc(-c3ccc(F)c(C)c3)cn2CCN2CCC2)CC1]

The reaction mixture of 6-chloro-5-ethyl-pyrimidin-4-ylamine (30.0 mg; 0.19 mmol; 1.0 eq.), 4-[1-(2-azetidin-1-yl-ethyl)-4-(4-fluoro-3-methyl-phenyl)-1H-imidazol-2-yl]-piperidine trihydrochloride (86.0 mg; 0.19 mmol; 1.0 eq.), and $Cs_2CO_3$ (310.1 mg; 0.95 mmol; 5.0 eq.) in DMSO (1.5 ml) was stirred at 120° C. for 48 hr. The crude was purified by prep HPLC to afford the title compound. LC-MS (M+H=464, obsd=464). $^1$H NMR (400 MHz, DMSO-d6) δ 8.49-8.39 (m, 1H), 8.10-8.01 (m, 1H), 7.96 (s, 1H), 7.93-7.85 (m, 1H), 7.50 (t, J=8.9 Hz, 1H), 6.69-6.61 (m, 2H), 4.30 (q, J=5.4, 4.7 Hz, 2H), 2.71-2.62 (m, 2H), 3.93 (d, J=12.5 Hz, 2H), 3.54 (q, J=6.3, 5.8 Hz, 4H), 3.33 (t, J=12.5 Hz, 3H), 3.11 (q, J=5.3, 4.0 Hz, 2H), 2.33 (dd, J=28.0, 11.5 Hz, 6H), 1.54 (q, J=6.7, 6.0 Hz, 3H).

6-{4-[1-(2-Azetidin-1-yl-ethyl)-4-(4-fluoro-3-methyl-phenyl)-1H-imidazol-2-yl]-piperidin-1-yl}-5-chloro-pyrimidin-4-ylamine (2)

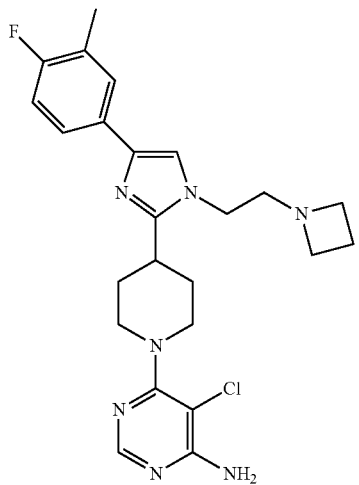 [SMILES: Cc1cc(-c2cn(CCN3CCC3)c(C3CCN(c4ncnc(N)c4Cl)CC3)n2)ccc1F]

The title compound was prepared according to the procedure described for the preparation of compound "1" by using 4-[1-(2-azetidin-1-yl-ethyl)-4-(4-fluoro-3-methyl-phenyl)-1H-imidazol-2-yl]-piperidine hydrochloride and 5,6-dichloro-pyrimidin-4-ylamine as starting materials. LC-MS (M+H=471, obsd=471). $^1$H NMR (400 MHz, DMSO-d6) δ 8.00 (s, 1H), 7.66-7.58 (m, 1H), 7.53 (ddd, J=7.8, 5.0, 2.3 Hz, 1H), 7.47 (s, 1H), 7.06 (dd, J=9.7, 8.6 Hz, 1H), 6.79 (s, 2H), 4.13 (d, J=13.0 Hz, 2H), 3.88 (t, J=6.2 Hz, 2H), 3.11 (t, J=6.9 Hz, 4H), 3.07-2.93 (m, 3H), 2.69 (t, J=6.1 Hz, 2H), 2.29-2.19 (m, 3H), 2.01-1.81 (m, 6H).

6-{4-[1-(2-Azetidin-1-yl-ethyl)-4-(2-isopropyl-pyridin-4-yl)-1H-imidazol-2-yl]-piperidin-1-yl}-5-isopropyl-pyrimidin-4-ylamine (3)

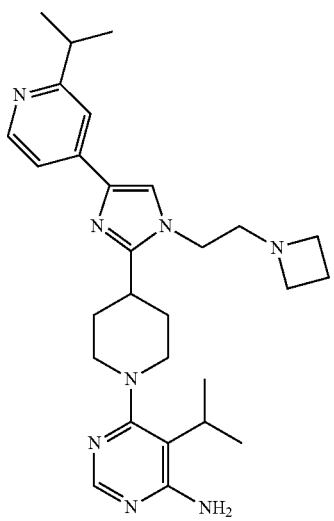 [SMILES: CC(C)c1cc(-c2cn(CCN3CCC3)c(C3CCN(c4ncnc(N)c4C(C)C)CC3)n2)ccn1]

The title compound was prepared according to the procedure described for the preparation of compound "1" by using 4-[1-(2-azetidin-1-yl-ethyl)-2-piperidin-4-yl-1H-imidazol-4-yl]-2-isopropyl-pyridine and 6-chloro-5-isopropyl-pyrimidin-4-ylamine as the starting materials. LC-MS (M+H=490, obsd=490). $^1$H NMR (400 MHz, DMSO-d6) δ 8.39 (t, J=3.9 Hz, 1H), 8.03 (t, J=2.1 Hz, 1H), 7.80 (d, J=2.9 Hz, 1H), 7.54 (s, 1H), 7.52-7.42 (m, 1H), 6.10 (s, 2H), 3.92 (d, J=6.4 Hz, 2H), 3.37 (s, 1H), 3.18-3.06 (m, 4H), 3.02 (q, J=7.5 Hz, 1H), 2.90 (t, J=11.7 Hz, 3H), 2.72 (d, J=6.5 Hz, 2H), 2.01-1.81 (m, 5H), 1.36-1.17 (m, 11H).

6-{4-[1-(2-Azetidin-1-yl-ethyl)-4-(4-fluoro-3-methyl-phenyl)-1H-imidazol-2-yl]-piperidin-1-yl}-5-isopropyl-pyrimidin-4-ylamine (4)

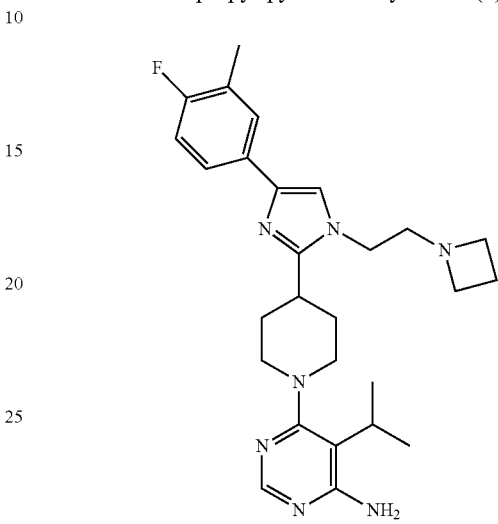

The mixture of 4-[1-(2-Azetidin-1-yl-ethyl)-4-(4-fluoro-3-methyl-phenyl)-1H-imidazol-2-yl]-piperidine (162.8 mg; 0.47 mmol; 1.0 eq.), 6-chloro-5-isopropyl-pyrimidin-4-ylamine (81.6 mg; 0.47 mmol; 1.0 eq.) and potassium carbonate (82.1 m g; 0.59 mmol; 1.25 eq.) in DMSO (3 ml) was stirred 120° C. for 56 hr. The crude was purified by prep HPLC to afford the title compound. LC-MS (M+H=478, obsd=478). $^1$H NMR (400 MHz, DMSO-d6) δ 8.02 (s, 1H), 7.66-7.59 (m, 1H), 7.54 (ddd, J=7.7, 4.9, 2.1 Hz, 1H), 7.48 (s, 1H), 7.08 (t, J=9.1 Hz, 1H), 6.13 (s, 2H), 3.87 (t, J=6.2 Hz, 2H), 3.11 (t, J=6.9 Hz, 4H), 2.93-2.80 (m, 3H), 2.68 (t, J=6.2 Hz, 2H), 2.30-2.21 (m, 3H), 1.92 (dtd, J=24.6, 12.8, 12.1, 4.0 Hz, 5H), 1.30 (d, J=7.2 Hz, 6H).

6-{4-[1-(2-Azetidin-1-yl-ethyl)-4-(2-trifluoromethyl-pyridin-4-yl)-1H-imidazol-2-yl]-piperidin-1-yl}-5-isopropyl-pyrimidin-4-ylamine (5)

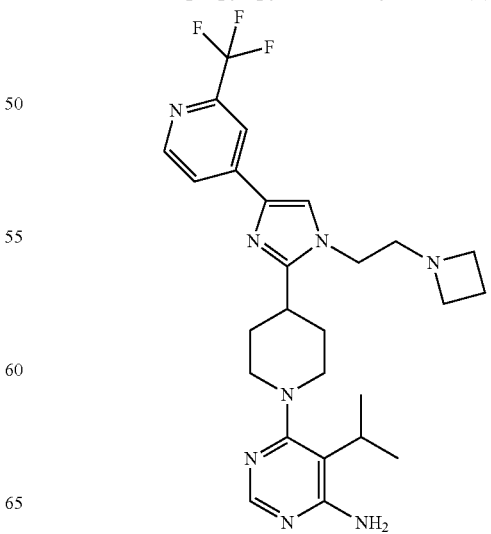

The title compound was prepared according to the procedure described for the preparation of compound "4" by using 4-[1-(2-azetidin-1-yl-ethyl)-2-piperidin-4-yl-1H-imidazol-4-yl]-2-trifluoromethyl-pyridine and 6-chloro-5-isopropyl-pyrimidin-4-ylamine as the starting materials. LC-MS (M+H=515, obsd.=515). $^1$H NMR (400 MHz, DMSO-d6) δ 8.65 (s, 1H), 8.16-8.01 (m, 6H), 7.97 (d, J=5.2 Hz, 2H), 6.11 (s, 4H), 3.94 (t, J=6.2 Hz, 4H), 3.46-3.25 (m, 4H), 3.12 (t, J=7.0 Hz, 8H), 2.92 (qd, J=12.0, 4.3 Hz, 7H), 2.72 (t, J=6.1 Hz, 4H), 2.03-1.84 (m, 13H), 1.30 (d, J=7.2 Hz, 13H).

5-Chloro-6-{4-[4-(4-fluoro-3-methyl-phenyl)-1-(1-methyl-azetidin-3-ylmethyl)-1H-imidazol-2-yl]-piperidin-1-yl}-pyrimidin-4-ylamine (6)

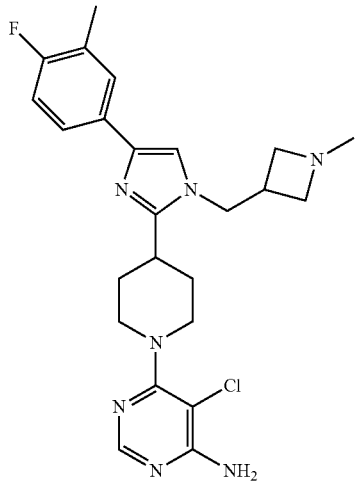 [SMILES: Cc1cc(-c2cn(CC3CN(C)C3)c(C3CCN(c4ncnc(N)c4Cl)CC3)n2)ccc1F]

The title compound was prepared according to the procedure described for the preparation of compound "1" by using 4-[4-(4-fluoro-3-methyl-phenyl)-1-(1-methyl-azetidin-3-ylmethyl)-1H-imidazol-2-yl]-piperidine and 5,6-Dichloro-pyrimidin-4-ylamine. LC-MS (M+H=471, obsd=471).

6-{4-[1-(2-Azetidin-1-yl-ethyl)-4-(4-fluoro-3-methyl-phenyl)-1H-imidazol-2-yl]-piperidin-1-yl}-5-(2H-pyrazol-3-yl)-pyrimidin-4-ylamine (7)

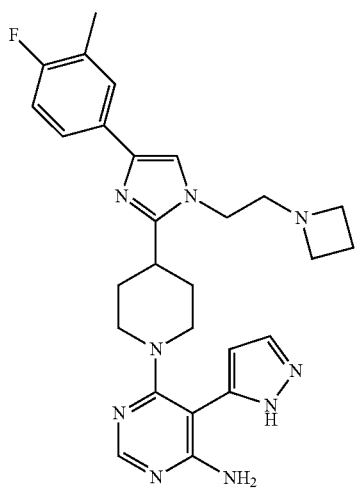 [SMILES: Cc1cc(-c2cn(CCN3CCC3)c(C3CCN(c4ncnc(N)c4-c4ccn[nH]4)CC3)n2)ccc1F]

Step 1: 6-{4-[1-(2-Azetidin-1-yl-ethyl)-4-(4-fluoro-3-methyl-phenyl)-1H-imidazol-2-yl]-piperidin-1-yl}-5-bromo-pyrimidin-4-ylamine The reaction mixture of 5-bromo-6-chloro-pyrimidin-4-ylamine (215.00 mg; 1.03 mmol; 1.0 eq.), 4-[1-(2-azetidin-1-yl-ethyl)-4-(4-fluoro-3-methyl-phenyl)-1H-imidazol-2-yl]-piperidine tetrahydrochloride (503.6 mg; 1.03 mmol; 1 eq.), and Cs$_2$CO$_3$ (1344.27 mg; 4.13 mmol; 4 eq.) in DMSO (1.5 ml) was stirred at 120° C. overnight. After cooling, the reaction mixture was poured into water. The precipitate was collected by filtration to yield the title compound as a yellow solid.

Step 2: 5-(4-Amino-6-{4-[1-(2-azetidin-1-yl-ethyl)-4-(4-fluoro-3-methyl-phenyl)-1H-imidazol-2-yl]-piperidin-1-yl}-pyrimidin-5-yl)-pyrazole-1-carboxylic acid tert-butyl ester The mixture of 6-{4-[1-(2-azetidin-1-yl-ethyl)-4-(4-fluoro-3-methyl-phenyl)-1H-imidazol-2-yl]-piperidin-1-yl}-5-bromo-pyrimidin-4-ylamine (90.00 mg; 0.17 mmol; 5-(4,4,5,5-tetramethyl-[1,3,2]dioxaborolan-2-yl)-pyrazole-1-carboxylic acid tert-butyl ester (61.75 mg; 0.21 mmol; and Cs$_2$CO$_3$ (114.00 mg; 0.35 mmol; in dioxane (5 ml) and water (0.5 ml) was purged with argon, and then added Pd (0) (t-Bu$_3$)$_2$ (6.26 mg; 0.01 mmol; 0.07 eq.). The resulting mixture was stirred at 50° C. overnight. The curde was purified by prep HPLC to afford the title compound.

Step 3: 6-{4-[1-(2-Azetidin-1-yl-ethyl)-4-(4-fluoro-3-methyl-phenyl)-1H-imidazol-2-yl]-piperidin-1-yl}-5-(2H-pyrazol-3-yl)-pyrimidin-4-ylamine To a solution of 5-(4-amino-6-{4-[1-(2-azetidin-1-yl-ethyl)-4-(4-fluoro-3-methyl-phenyl)-1H-imidazol-2-yl]-piperidin-1-yl}-pyrimidin-5-yl)-pyrazole-1-carboxylic acid tert-butyl ester (1.00 eq.) in DCM (1 ml), was added trifluoro-acetic acid (0.5 ml). The reaction mixture was stirred at RT for 30 min. After removal of the solvent, the crude was purified by HPLC to yield the title compound. LC-MS (M+H=502, obsd=502).

6-{4-[1-(2-Azetidin-1-yl-ethyl)-4-(4-fluoro-3-methyl-phenyl)-1H-imidazol-2-yl]-piperidin-1-yl}-5-pyridin-4-yl-pyrimidin-4-ylamine (8)

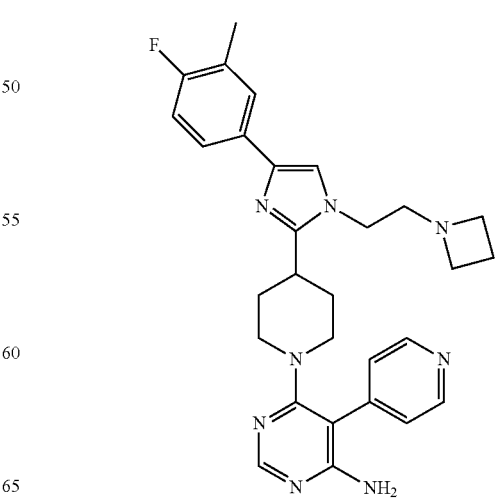

The mixture of 6-{4-[1-(2-azetidin-1-yl-ethyl)-4-(4-fluoro-3-methyl-phenyl)-1H-imidazol-2-yl]-piperidin-1-yl}-5-bromo-pyrimidin-4-ylamine (90.00 mg; 0.17 mmol; 1.00 eq.), pyridin-4-ylboronic acid (25.81 mg; 0.21 mmol; 1.20 eq.) and Cs$_2$CO$_3$ (114.00 mg; 0.35 mmol; 2.00 eq.) in dioxane (2 ml) and water (0.2 ml) was purged with argon, and then Pd (0) (t-Bu$_3$)$_2$ (6.26 mg; 0.01 mmol; 0.07 eq.) was added. The resulting mixture was stirred at 50° C. overnight. The crude was purified by HPLC twice (first by basic condition and then acidic condition) to afford the title compound as TFA salt. LC-MS (M+H=513, obsd=513).

6-{4-[1-(2-Azetidin-1-yl-ethyl)-4-(4-fluoro-3-methyl-phenyl)-1H-imidazol-2-yl]-piperidin-1-yl}-5-pyridin-3-yl-pyrimidin-4-ylamine (9)

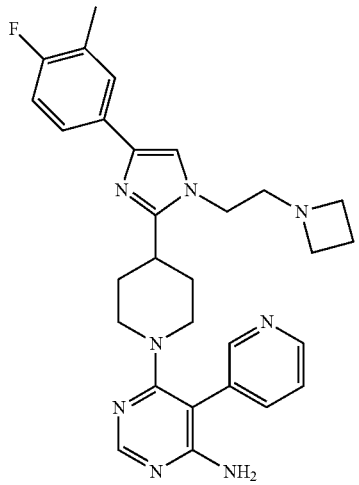 [SMILES: Cc1cc(-c2cn(CCN3CCC3)c(C3CCN(c4ncnc(N)c4-c4cccnc4)CC3)n2)ccc1F]

The title compound was prepared according to the procedure described for the preparation of compound "8" by using 6-{4-[1-(2-azetidin-1-yl-ethyl)-4-(4-fluoro-3-methyl-phenyl)-1H-imidazol-2-yl]-piperidin-1-yl}-5-bromo-pyrimidin-4-ylamine and pyridin-3-ylboronic acid as the starting materials. LC-MS (M+H=513, obsd=513).

6-{4-[1-(2-Azetidin-1-yl-ethyl)-4-(2-isopropyl-pyridin-4-yl)-1H-imidazol-2-yl]-piperidin-1-yl}-5-ethoxy-pyrimidin-4-ylamine (10)

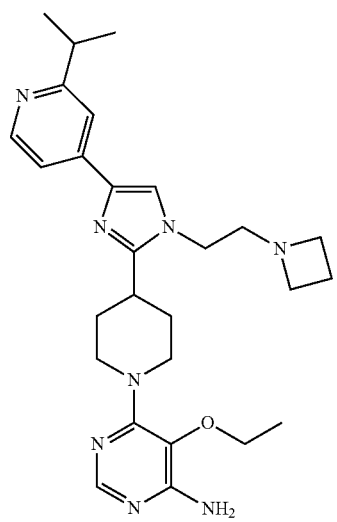 [SMILES: CCOc1c(N)ncnc1N1CCC(c2nc(-c3ccnc(C(C)C)c3)cn2CCN2CCC2)CC1]

The title compound was prepared according to the procedure described for the preparation of compound "1" by using 4-[1-(2-azetidin-1-yl-ethyl)-2-piperidin-4-yl-1H-imidazol-4-yl]-2-isopropyl-pyridine and 6-chloro-5-ethoxy-pyrimidin-4-ylamine as the starting materials. LC-MS (M+H=491, obsd=491).

6-{4-[1-(2-Azetidin-1-yl-ethyl)-4-(2-isopropyl-pyridin-4-yl)-1H-imidazol-2-yl]-piperidin-1-yl}-5-cyclobutyl-pyrimidin-4-ylamine (11)

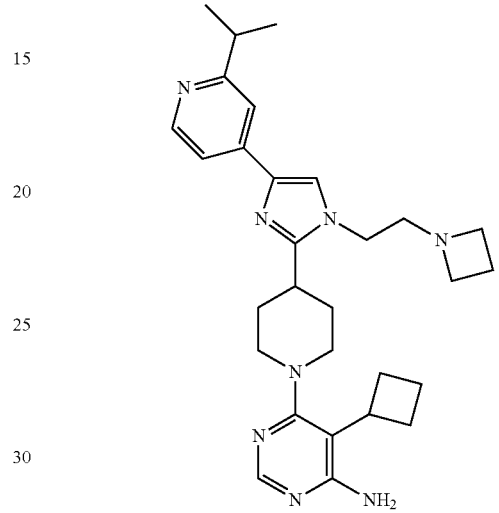

The title compound was prepared according to the procedure described for the preparation of compound "1" by using 4-[1-(2-azetidin-1-yl-ethyl)-2-piperidin-4-yl-1H-imidazol-4-yl]-2-isopropyl-pyridine and 6-chloro-5-cyclobutyl-pyrimidin-4-ylamine as the starting materials. LC-MS (M+H=501, obsd=501).

6-{4-[1-(2-Azetidin-1-yl-ethyl)-4-(2-isopropyl-pyridin-4-yl)-1H-imidazol-2-yl]-piperidin-1-yl}-5-isopropoxy-pyrimidin-4-ylamine (12)

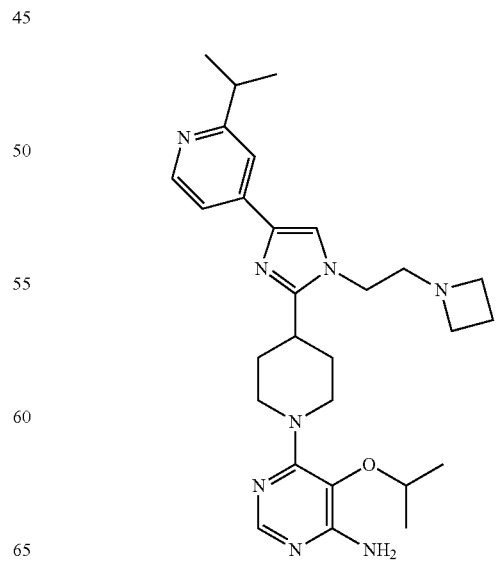

The title compound was prepared according to the procedure described for the preparation of compound "1" by using 4-[1-(2-azetidin-1-yl-ethyl)-2-piperidin-4-yl-1H-imidazol-4-yl]-2-isopropyl-pyridine and 6-chloro-5-isopropoxy-pyrimidin-4-ylamine as the starting materials. LC-MS (M+H=505, obsd=505).

6-{4-[1-(2-Azetidin-1-yl-ethyl)-4-(2-isopropyl-pyridin-4-yl)-1H-imidazol-2-yl]-piperidin-1-yl}-5-Pyridin-4-yl-pyrimidin-4-ylamine (13)

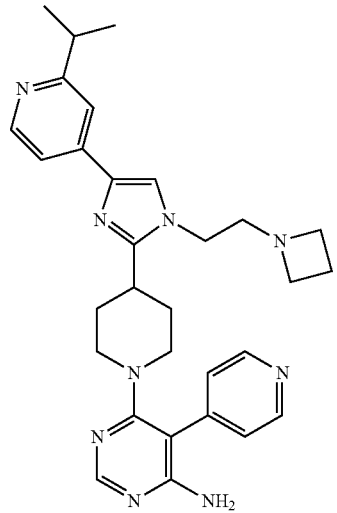 [SMILES: CC(C)c1cc(-c2cn(CCN3CCC3)c(C3CCN(c4ncnc(N)c4-c4ccncc4)CC3)n2)ccn1]

The title compound was prepared according to the procedure described for the preparation of compound "8" by using 6-{4-[1-(2-azetidin-1-yl-ethyl)-4-(2-isopropyl-pyridin-4-yl)-1H-imidazol-2-yl]-piperidin-1-yl}-5-pyridin-4-yl-pyrimidin-4-ylamine and 4-pyridinylboronic acid as the starting materials. LC-MS (M+H=524, obsd=524).

6-{4-[1-(2-Azetidin-1-yl-ethyl)-4-(2-isopropyl-pyridin-4-yl)-1H-imidazol-2-yl]-piperidin-1-yl}-5-(2,2,2-trifluoro-ethoxy)-Pyrimidin-4-ylamine (14)

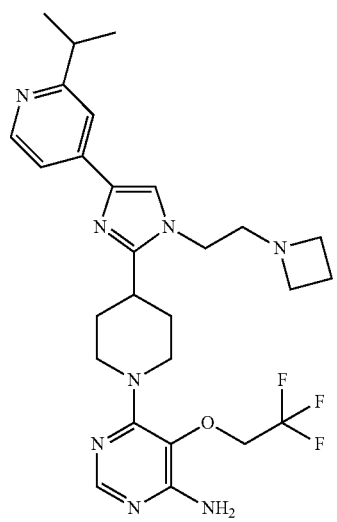 [SMILES: CC(C)c1cc(-c2cn(CCN3CCC3)c(C3CCN(c4ncnc(N)c4OCC(F)(F)F)CC3)n2)ccn1]

The title compound was prepared according to the procedure described for the preparation of compound "1" by using 4-[1-(2-azetidin-1-yl-ethyl)-2-piperidin-4-yl-1H-imidazol-4-yl]-2-isopropyl-pyridine and 6-chloro-5-(2,2,2-trifluoro-ethoxy)-pyrimidin-4-ylamine as the starting materials. LC-MS (M+H=545, obsd=545).

4-Amino-6-{4-[1-(2-azetidin-1-yl-ethyl)-4-(2-isopropyl-pyridin-4-yl)-1H-imidazol-2-yl]-piperidin-1-yl}-pyrimidine-5-carbaldehyde (15)

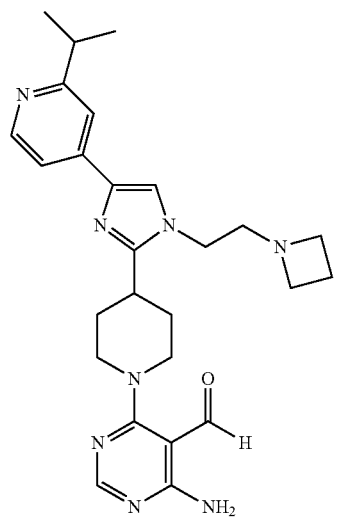

The title compound was prepared according to the procedure described for the preparation of compound "1" by using 4-[1-(2-azetidin-1-yl-ethyl)-2-piperidin-4-yl-1H-imidazol-4-yl]-2-isopropyl-pyridine and 6-chloro-5-difluoromethyl-pyrimidin-4-ylamine as the starting materials. LC-MS (M+H=475, obsd=475).

6-{4-[1-(2-Azetidin-1-yl-ethyl)-4-(4-fluoro-3-methyl-phenyl)-1H-imidazol-2-yl]-piperidin-1-yl}-5-cyclopropyl-pyrimidin-4-ylamine (16)

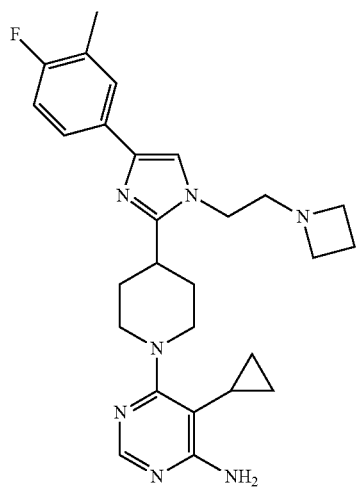 [SMILES: Cc1cc(-c2cn(CCN3CCC3)c(C3CCN(c4ncnc(N)c4C4CC4)CC3)n2)ccc1F]

The title compound was prepared according to the procedure described for the preparation of compound "1" by using 4-[1-(2-azetidin-1-yl-ethyl)-4-(4-fluoro-3-methyl-phenyl)-1H-imidazol-2-yl]-piperidine trihydrochloride and 6-chloro-5-cyclopropyl-pyrimidin-4-ylamine as the starting materials. LC-MS (M+H=476, obsd=476). ¹H NMR (400 MHz, DMSO-d6) δ 7.92 (s, 1H), 7.66-7.56 (m, 1H), 7.55-7.49 (m, 1H), 7.47 (s, 1H), 7.07 (t, J=9.1 Hz, 1H), 6.16 (s, 2H), 4.19 (d, J=13.0 Hz, 2H), 3.88 (t, J=6.3 Hz, 2H), 3.11 (t, J=6.9 Hz, 4H), 3.05-2.86 (m, 3H), 2.69 (t, J=6.2 Hz, 2H), 2.26 (s, 3H), 1.92 (ddt, J=26.3, 10.1, 5.7 Hz, 6H), 1.49 (q, J=6.9 Hz, 1H), 1.09-0.95 (m, 2H), 0.43 (d, J=5.2 Hz, 2H).

6-{4-[1-(2-Azetidin-1-yl-ethyl)-4-(2-isopropyl-pyridin-4-yl)-1H-imidazol-2-yl]-piperidin-1-yl}-5-cyclopropyl-pyrimidin-4-ylamine (17)

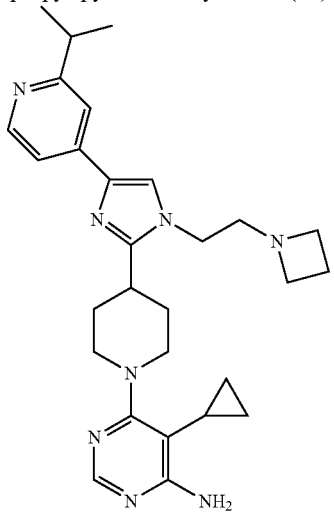

The title compound was prepared according to the procedure described for the preparation of compound "1" by using 4-[1-(2-azetidin-1-yl-ethyl)-2-piperidin-4-yl-1H-imidazol-4-yl]-2-isopropyl-pyridine and 6-chloro-5-cyclopropyl-pyrimidin-4-ylamine as the starting materials. LC-MS (M+H=487, obsd=487). ¹H NMR (400 MHz, DMSO-d6) δ 8.38 (d, J=5.2 Hz, 1H), 7.92 (s, 1H), 7.81 (s, 1H), 7.52 (s, 1H), 7.46 (d, J=5.2 Hz, 1H), 6.17 (s, 2H), 4.19 (d, J=12.9 Hz, 2H), 3.92 (t, J=6.1 Hz, 2H), 3.12 (t, J=6.7 Hz, 4H), 3.05-2.88 (m, 4H), 2.72 (t, J=6.1 Hz, 2H), 1.98-1.82 (m, 6H), 1.50 (p, J=6.7 Hz, 1H), 1.25 (dd, J=6.9, 1.3 Hz, 6H), 1.02 (d, J=8.1 Hz, 2H), 0.43 (d, J=5.2 Hz, 2H).

6-{4-[1-(2-Azetidin-1-yl-ethyl)-4-(2-isopropyl-pyridin-4-yl)-1H-imidazol-2-yl]-piperidin-1-yl}-5-phenyl-pyrimidin-4-ylamine (18)

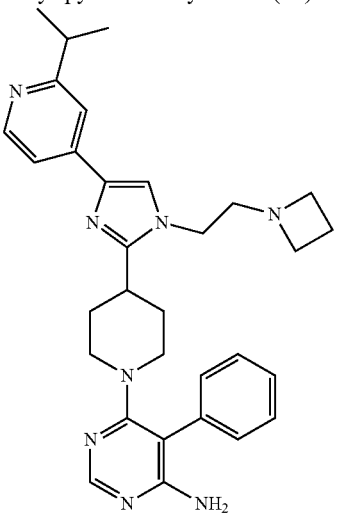

The title compound was prepared according to the procedure described for the preparation of compound "8" by using 6-{4-[1-(2-azetidin-1-yl-ethyl)-4-(2-isopropyl-pyridin-4-yl)-1H-imidazol-2-yl]-piperidin-1-yl}-5-bromo-pyrimidin-4-ylamine and benzenboronic acid as the starting materials. LC-MS (M+H=523, obsd=523). ¹H NMR (400 MHz, DMSO-d6) δ 8.37 (dd, J=5.1, 0.8 Hz, 1H), 8.08 (s, 1H), 7.76 (s, 1H), 7.54-7.46 (m, 3H), 7.43 (dd, J=5.1, 1.6 Hz, 1H), 7.36 (dddd, J=9.9, 6.5, 2.9, 1.6 Hz, 3H), 5.65 (s, 2H), 3.83 (t, J=6.2 Hz, 2H), 3.79-3.66 (m, 2H), 3.09 (t, J=7.0 Hz, 4H), 3.00 (h, J=6.9 Hz, 1H), 2.92-2.79 (m, 1H), 2.69 (dd, J=20.7, 7.0 Hz, 1H), 1.92 (p, J=7.0 Hz, 2H), 1.59 (dt, J=8.0, 4.5 Hz, 4H), 1.25 (d, J=6.9 Hz, 6H).

6-{4-[1-(2-Azetidin-1-yl-ethyl)-4-(2-isopropyl-pyridin-4-yl)-1H-imidazol-2-yl]-piperidin-1-yl}-5-Pyridin-3-yl-pyrimidin-4-ylamine (19)

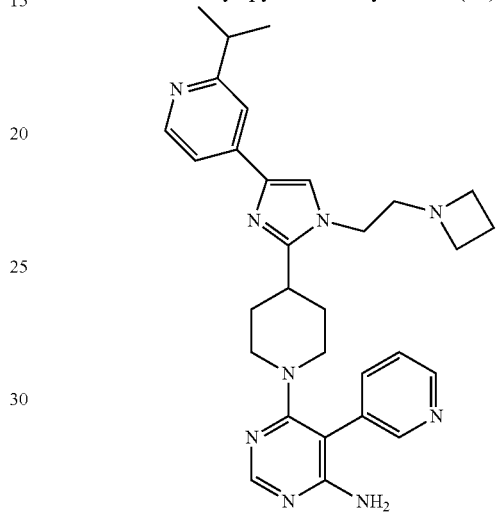

The title compound was prepared according to the procedure described for the preparation of compound "8" by using 6-{4-[1-(2-azetidin-1-yl-ethyl)-4-(2-isopropyl-pyridin-4-yl)-1H-imidazol-2-yl]-piperidin-1-yl}-5-bromo-pyrimidin-4-ylamine and 3-pyridinylboronic acid as the starting materials. LC-MS (M+H=524, obsd=524). ¹H NMR (400 MHz, DMSO-d6) δ 8.59-8.50 (m, 2H), 8.38 (dd, J=5.1, 0.8 Hz, 1H), 8.11 (s, 1H), 7.80-7.72 (m, 2H), 7.53-7.47 (m, 2H), 7.43 (dd, J=5.1, 1.6 Hz, 1H), 5.92 (s, 2H), 3.85 (t, J=6.1 Hz, 2H), 3.40-3.27 (m, 5H), 3.63 (d, J=3.1 Hz, 1H), 3.12 (s, 5H), 3.01 (p, J=6.9 Hz, 1H), 2.85 (dt, J=10.1, 5.0 Hz, 1H), 2.77-2.63 (m, 4H), 2.01-1.87 (m, 2H), 1.65-1.52 (m, 4H), 1.25 (d, J=6.9 Hz, 6H).

5-Ethoxy-6-{4-(3-chloro-4-fluorophenyl)-1-2-(dimethylamino-1-yl-ethyl)-1H-imidazol-2-yl]-piperidin-1-yl}-pyrimidin-4-ylamine (20)

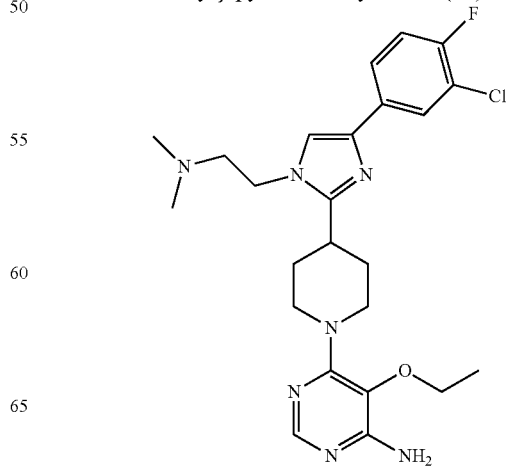

The title compound was prepared according to the procedure described for the preparation of compound "1" by using 4-[4-(3-chloro-4-fluoro-phenyl)-1-(2-dimethylamino-1-yl-ethyl)-1H-imidazol-2-yl]-piperidine and 6-chloro-5-ethoxy-pyrimidin-4-ylamine as the starting materials. LC-MS (M+H=489, obsd=489). ¹H NMR (400 MHz, DMSO-d6) δ 1.29 (t, 3H), 1.89 (m, 4H), 2.21 (m, 5H), 2.60 (m, 3H), 2.97 (m, 3H), 3.80 (q, 2H), 4.03 (m, 4H), 6.79 (2H), 7.46 (m, 1H), 7.75 (s, 1H), 7.99 (1H), 8.03 (s, 1H).

5-Bromo-6-{4-(3-methyl-4-fluorophenyl)-1-2-(dimethylamino-1-yl-ethyl)-1H-imidazol-2-yl]-piperidin-1-yl}-pyrimidin-4-ylamine (21)

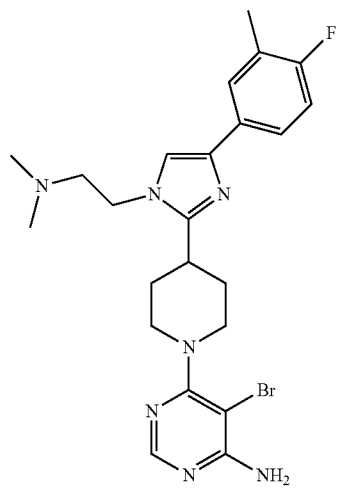 [SMILES: Cc1cc(-c2cn(CCN(C)C)c(C3CCN(c4ncnc(N)c4Br)CC3)n2)ccc1F]

The title compound was prepared according to the procedure described for the preparation of compound "1" by using 4-[4-(3-methyl-4-fluoro-phenyl)-1-(2-dimethylamino-1-yl-ethyl)-1H-imidazol-2-yl]-piperidine and 5-bromo-6-chloro-pyrimidin-4-ylamine as the starting materials. LC-MS (M+H=502, obsd=502). ¹H NMR (400 MHz, DMSO-d6) δ 1.88 (m, 4H), 2.21 (s, 4H), 2.25 (s, 3H), 2.51 (m, 3H), 2.57 (m, 2H), 2.97 (m, 2H), 4.03 (m, 4H), 6.77 (s, 2H), 7.06 (t, 1H), 7.50 (m, 2H), 7.63 (m, 1H), 8.03 (s, 1H).

5-Chloro-6-{4-(3-methyl-4-fluorophenyl)-1-2-(dimethylamino-1-yl-ethyl)-1H-imidazol-2-yl]-piperidin-1-yl}-pyrimidin-4-ylamine (22)

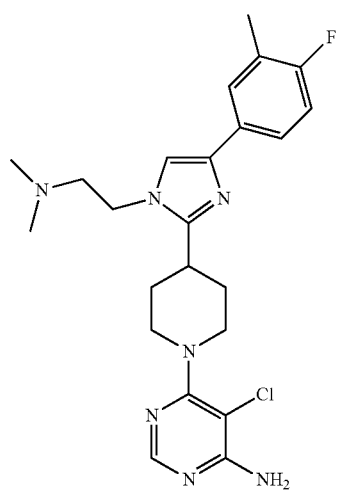 [SMILES: Cc1cc(-c2cn(CCN(C)C)c(C3CCN(c4ncnc(N)c4Cl)CC3)n2)ccc1F]

The title compound was prepared according to the procedure described for the preparation of compound "1" by using 4-[4-(3-methyl-4-fluoro-phenyl)-1-(2-dimethylamino-1-yl-ethyl)-1H-imidazol-2-yl]-piperidine and 5,6-dichloro-pyrimidin-4-ylamine as the starting materials. LC-MS (M+H=458, obsd=458). ¹H NMR (400 MHz, DMSO-d6) δ 1.88 (m, 4H), 2.21 (s, 4H), 2.25 (s, 3H), 2.58 (m, 3H), 2.58 (m, 2H), 3.02 (m, 2H), 4.03 (m, 2H), 4.13 (m, 2H), 6.79 (s, 2H), 7.06 (t, 1H), 7.49 (m, 2H), 7.61 (m, 1H), 8.03 (s, 1H).

5-Chloro-6-{4-(3-trifluoromethyl-4-fluorophenyl)-1-2-(dimethylamino-1-yl-ethyl)-1H-imidazol-2-yl]-piperidin-1-yl}-pyrimidin-4-ylamine (23)

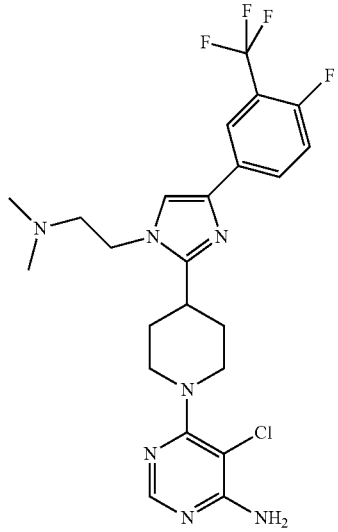 [SMILES: CN(C)CCn1cc(-c2ccc(F)c(C(F)(F)F)c2)nc1C1CCN(c2ncnc(N)c2Cl)CC1]

The title compound was prepared according to the procedure described for the preparation of compound "1" by using 4-[4-(3-trifluoro-4-fluoro-phenyl)-1-(2-dimethylamino-1-yl-ethyl)-1H-imidazol-2-yl]-piperidine and 5,6-dichloro-pyrimidin-4-ylamine as the starting materials. LC-MS (M+H=512, obsd=512). ¹H NMR (400 MHz, DMSO-d6) δ 1.89 (m, 4H), 2.21 (m, 5H), 2.60 (m, 3H), 2.97 (m, 3H), 4.03 (m, 4H), 6.79 (2H), 7.46 (m, 1H), 7.75 (s, 1H), 7.99 (1H), 8.03 (s, 1H).

5-Chloro-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (24)

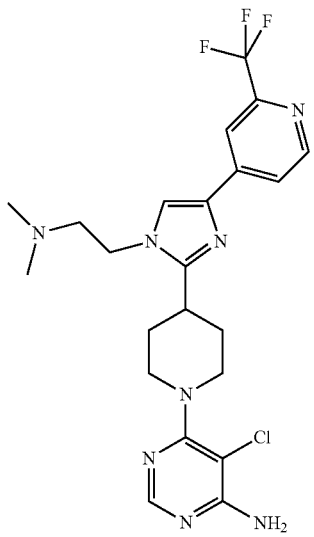 [SMILES: CN(C)CCn1cc(-c2ccnc(C(F)(F)F)c2)nc1C1CCN(c2ncnc(N)c2Cl)CC1]

The title compound was prepared according to the procedure described for the preparation of compound "1" by using 4-(3-trifluoromethyl-pyridin-4-yl)-1-2-(dimethyl-amino-1-yl-ethyl)-1H-imidazol-2-yl]-piperidine and 5,6-dichloro-pyrimidin-4-ylamine as the starting materials. LC-MS (M+H=495, obsd=495). ¹H NMR (400 MHz, DMSO-d6) δ 1.90 (m, 4H), 2.21 (m, 6H), 2.60 (m, 2H), 2.99 (m, 4H), 4.03 (m, 4H), 6.80 (2H), 7.97 (m, 1H), 8.00 (s, 1H), 8.07 (2H), 8.64 (m, 1H).

5-Bromo-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (25)

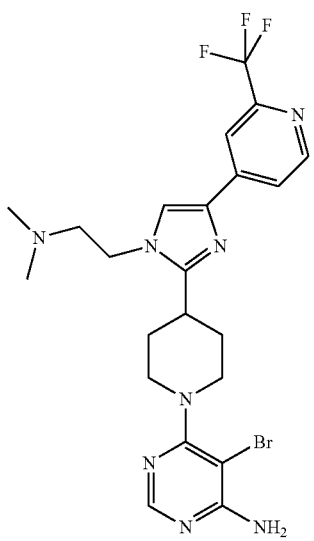 [SMILES: CN(C)CCn1cc(-c2ccnc(C(F)(F)F)c2)nc1C1CCN(c2ncnc(N)c2Br)CC1]

The title compound was prepared according to the procedure described for the preparation of compound "1" by using 4-(3-trifluoromethyl-pyridin-4-yl)-1-2-(dimethyl-amino-1-yl-ethyl)-1H-imidazol-2-yl]-piperidine and 5-bromo-6-chloro-pyrimidin-4-ylamine as the starting materials. LC-MS (M+H=539, obsd=539). ¹H NMR (400 MHz, DMSO-d6) δ 1.87 (m, 4H), 2.21 (s, 6H), 2.62 (m, 2H), 3.05 (m, 3H), 4.02-4.11 (m, 5H), 6.78 (s, 2H), 7.94 (m, 1H), 8.02 (s, 1H), 8.09 (2H), 8.64 (m, 1H).

5-Ethoxy-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (26)

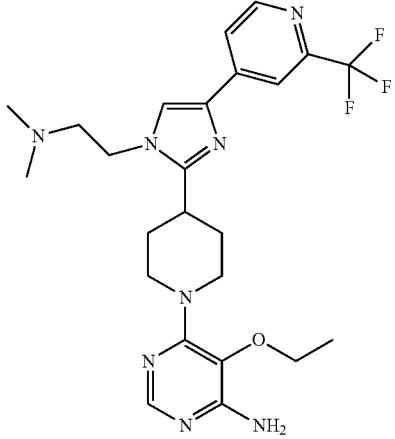 [SMILES: CCOc1c(N)ncnc1N1CCC(c2nc(-c3ccnc(C(F)(F)F)c3)cn2CCN(C)C)CC1]

The title compound was prepared according to the procedure described for the preparation of compound "1" by using 4-(3-trifluoromethyl-pyridin-4-yl)-1-2-(dimethyl-amino-1-yl-ethyl)-1H-imidazol-2-yl]-piperidine and 6-chloro-5-ethoxy-pyrimidin-4-ylamine as the starting materials. LC-MS (M+H=505, obsd=505). ¹H NMR (400 MHz, DMSO-d6) δ 1.29 (t, 3H), 1.87 (m, 4H), 2.21 (s, 6H), 2.61 (m, 2H), 2.99 (m, 3H), 3.80 (m, 2H), 4.09 (m, 2H), 4.42 (m, 2H), 6.17 (s, 2H), 7.80 (s, 1H), 7.93 (m, 1H), 8.08 (m, 2H), 8.63 (m, 1H).

5-Ethyl-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (27)

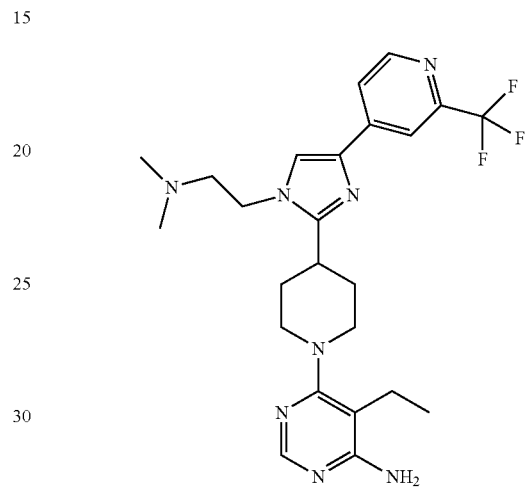

The title compound was prepared according to the procedure described for the preparation of compound "1" by using 4-(3-trifluoromethyl-pyridin-4-yl)-1-2-(dimethyl-amino-1-yl-ethyl)-1H-imidazol-2-yl]-piperidine and 6-chloro-5-ethyl-pyrimidin-4-ylamine as the starting materials. LC-MS (M+H=489, obsd=489). ¹H NMR (400 MHz, DMSO-d6) δ 1.10 (3H), 1.87 (m, 2H), 2.21 (s, 6H), 2.64 (m, 2H), 2.92 (m, 2H), 3.49 (m, 2H), 4.08 (m, 2H), 6.25 (s, 2H), 7.96 (m, 1H), 8.01 (s, 1H), 8.09 (2H), 8.66 (m, 1H).

5-Isoproxy-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (28)

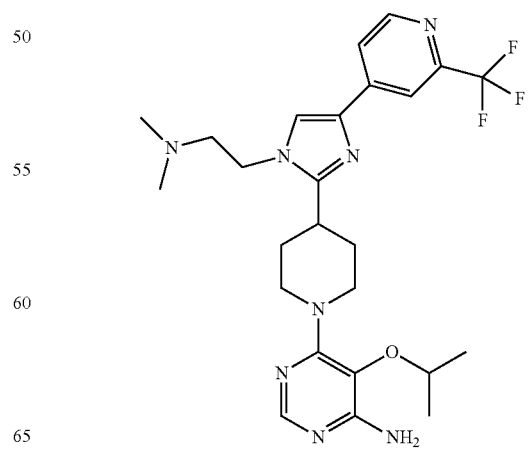

The title compound was prepared according to the procedure described for the preparation of compound "1" by using 4-(3-trifluoromethyl-pyridin-4-yl)-1-2-(dimethyl-amino-1-yl-ethyl)-1H-imidazol-2-yl]-piperidine and 6-chloro-5-isoproxy-pyrimidin-4-ylamine as the starting materials. LC-MS (M+H=519, obsd=519). $^1$H NMR (400 MHz, DMSO-d6) δ 1.21 (d, 6H), 1.87 (m,4H), 2.21 (s, 6H), 2.64 (m, 2H),2.92 (m, 2H), 3.05 (m, 1H), 4.09 (m, 2H),4.33 (m, 2H), 6.11 (s, 2H), 7.81 (s, 1H), 7.94 (m, 1H), 8.08 (m, 2H), 8.64 (m, 1H).

4-amino-6-{4-(3-trifluoromethyl-pyridin-4-yl)-1-2-(dimethylamino-1-yl-ethyl)-1H-imidazol-2-yl]-piperidin-1-yl}-pyrimidin-5-carbonitrile (29)

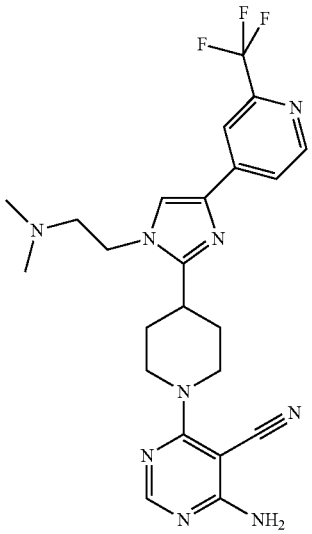 [SMILES: CN(C)CCn1cc(-c2ccnc(C(F)(F)F)c2)nc1C1CCN(c2ncnc(N)c2C#N)CC1]

The reaction mixture of dimethyl-{2-[2-piperidin-4-yl-4-(2-trifluoromethyl-pyridin-4-yl)-imidazol-1-yl]-ethyl}-amine dihydrochloride (200.0 mg; 0.45 mmol; 1.0 eq.), 4-amino-6-chloro-pyrimidine-5-carbonitrile (70.2 mg; 0.45 mmol; 1.0 eq.) and potassium carbonate (627.7 mg; 4.54 mmol; 10.0 eq.) in anhydrous DMF (5 mL) was stirred at 60° C. overnight. After cooling, the reaction mixture was poured into water. The precipitate was collected by filtration to yield the title compound. LC-MS (M+H=486, obsd=486). $^1$H NMR (400 MHz, DMSO-d6) δ 1.88-1.93 (m, 4H), 2.22 (s, 6H), 2.62 (m, 2H), 3.25 (m, 3H), 4.09 (m, 2H), 4.63 (m, 2H), 7.30 (s, 2H), 7.93 (m, 1H), 8.07 (m, 3H), 8.64 (m, 1H).

4-amino-6-{4-(3-trifluoromethyl-pyridin-4-yl)-1-2-(dimethylamino-1-yl-ethyl)-1H-imidazol-2-yl]-piperidin-1-yl}-pyrimidin-5-carboxamide (30)

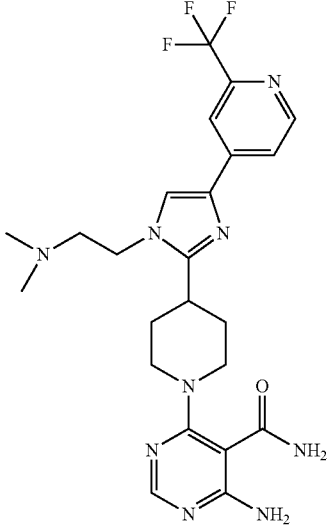 [SMILES: CN(C)CCn1cc(-c2ccnc(C(F)(F)F)c2)nc1C1CCN(c2ncnc(N)c2C(N)=O)CC1]

To the mixture of 4-amino-6-{4-[1-(2-dimethylamino-ethyl)-4-(2-trifluoromethyl-pyridin-4-yl)-1H-imidazol-2-yl]-piperidin-1-yl}-pyrimidine-5-carbonitrile (90.0 mg; 0.19 mmol; 1.0 eq.) and 2.0 M NaOH (0.46 ml; 0.93 mmol; 5.0 eq.) in DMSO (6 ml), hydrogen peroxide (0.03 ml; 0.37 mmol; 2.0 eq.) was added at room temperature. Then the mixture was stirred at rt for 60 min. The reaction mixture was purified by reverse phase HPLC to afford the title compound as a white solid. LC-MS (M+H=504, obsd=504). $^1$H NMR (400 MHz, DMSO-d6) δ 1.87 (m, 4H), 2.21 (s, 6H), 2.62 (m, 2H), 3.05 (m, 3H), 4.00 (m, 2H), 4.09 (m, 2H), 6.85 (s, 2H), 7.51 (s, 1H), 7.59 (s, 1H), 7.93 (m, 1H), 8.00 (s, 1H), 8.09 (2H), 8.64 (m, 1H).

6-{4-[1-(2-Ethylamino-ethyl)-4-(4-fluoro-3-trifluoromethyl-phenyl)-1H-imidazol-2-yl]-piperidin-1-yl}-5-isopropyl-pyrimidin-4-ylamine (31)

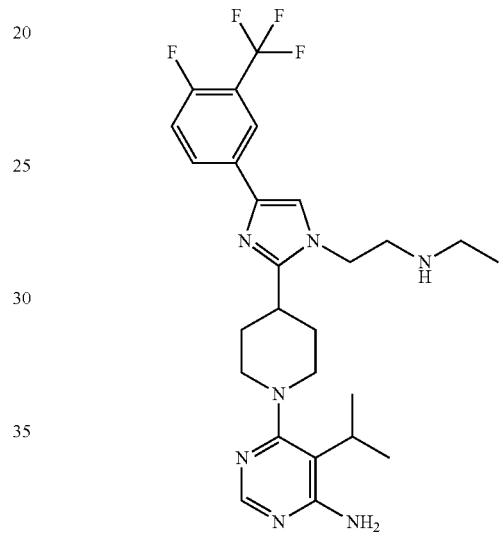

Step 1: {2-[2-[1-(6-Amino-5-isopropyl-pyrimidin-4-yl)-piperidin-4-yl]-4-(4-fluoro-3-trifluoromethyl-phenyl)-imidazol-1-yl]-ethyl}-ethyl-carbamic acid benzyl ester A reaction mixture of 6-chloro-5-isopropyl-pyrimidin-4-ylamine (40.0 mg; 0.23 mmol; 1.0 eq.), ethyl-{2-[4-(4-fluoro-3-trifluoromethyl-phenyl)-2-piperidin-4-yl-imidazol-1-yl]-ethyl}-carbamic acid benzyl ester trifluoroacetate (2) (174.0 mg; 0.23 mmol; 1.0 eq.), and Cs$_2$CO$_3$ (303.7 mg; 0.93 mmol; 4.0 eq.) in DMSO (1.5 ml) was stirred at 120° C. for 48 hr. The crude was purified by prep HPLC to yield the title compound.

Step 2: 6-{4-[1-(2-Ethylamino-ethyl)-4-(4-fluoro-3-trifluoromethyl-phenyl)-1H-imidazol-2-yl]-1-yl}-5-isopropyl-pyrimidin-4-ylamine A mixture of {2-[2-[1-(6-amino-5-isopropyl-pyrimidin-4-yl)-piperidin-4-yl]-4-(4-fluoro-3-trifluoromethyl-phenyl)-imidazol-1-yl]-ethyl}-ethyl-carbamic acid benzyl ester (30.0 mg; 0.05 mmol; 1.0 eq.) and trifluoroacetic acid (15.7 mg; 0.14 mmol; 3.0 eq.) in methanol (5 ml) was stirred for 10 min at RT, 30 mg of wet 10% Pd/C was then added, followed by ammonium formate (28.94 mg; 0.46 mmol; 10.00 eq.). The mixture was stirred at RT for 2 hr. LC-MS showed clean desired compound. After removal of catalyst and concentration, the residue was purified by prep HPLC to afford the title compound. LC-MS (M+H=520, obsd=520).

6-{4-[1-[2-(3-Chloro-propylamino)-ethyl]-4-(4-fluoro-3-methyl-phenyl)-1H-imidazol-2-yl]-piperidin-1-yl}-5-isopropyl-pyrimidin-4-ylamine (32)

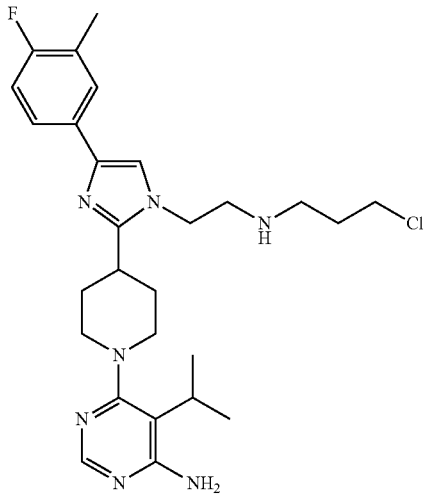 [SMILES: Cc1cc(-c2cn(CCNCCCCl)c(C3CCN(c4ncnc(N)c4C(C)C)CC3)n2)ccc1F]

To a solution of 6-{4-[1-(2-azetidin-1-yl-ethyl)-4-(4-fluoro-3-methyl-phenyl)-1H-imidazol-2-yl]-piperidin-1-yl}-5-isopropyl-pyrimidin-4-ylamine (70.0 mg; 0.15 mmol; 1.0 eq.) in methanol (0.5 ml), was added 4.0M HCl in dioxane (0.37 ml; 1.47 mmol; 10.0 eq.). The reaction mixture was stirred at 40° C. for 72 hr. After removal of the solvents, the crude was purified by prep HPLC to afford the title compound. LC-MS (M+H=515, obsd=515).

Biological Activity

P70S6K Enzyme Assay

P70S6K inhibitor compounds were diluted and plated in 96 well plates. A reaction mixture including the following components was then added to the compound plate to initiate the enzyme reaction; P70S6K (3 nM, T412E mutant, Millipore) was mixed with 24 µM ATP in an assay buffer containing 100 mM Hepes (pH 7.5), 5 mM MgCl2, 1 mM DTT, 0.015% Brij and 1 µM of the substrate peptide FITC-AHA-AKRRRLSSLRA-OH (derived from the S6 ribosomal protein sequence, FITC=fluorescein isothiocyanate, AHA=6-aminohexanoic acid). The reaction was incubated for 90 min at 25° C., before the addition of 10 mM EDTA to stop the reaction. The proportion of substrate and product (phosphorylated) peptide was analysed on a Caliper Life Sciences Lab Chip 3000, using a pressure of −1.4 psi, and upstream and downstream voltages of −3000 and −700 respectively. Product peaks were resolved before substrate peaks on the resulting chromatograms.

AKT Enzyme Assay

A TTP Mosquito liquid handling instrument was used to place 125 nl of the appropriate concentration of inhibitor in 100% DMSO (for a dose response curve calculation) into each well of a 384-well plate. To this reaction components were added to a final volume of 12.5 µl:

0.1 ng/µl His-AKT (Full Length), (Invitrogen, Part # P2999, Lot #641228C).
160 uM ATP (Fluka, 02055)
1 mM DTT (Sigma, D0632)
1 mM MgCl2 (Sigma, M1028)
1 µM substrate peptide (sequence FITC-AHA-GRPRTSS-FAEG-NH2), synthesized by Tufts Peptide Synthesis service.
100 mM HEPES pH 7.5 (Calbiochem, 391338)
0.015% Brij-35 (Sigma, B4184)

The reaction was incubated for 90 min at 25 C, and then stopped by the addition of 70 µl of Stop buffer (100 mM HEPES pH 7.5, 0.015% Brij-35, 10 mM EDTA (Sigma, E7889)).

The plate was read on a Caliper LC 3000 in an Off-Chip mobility shift assay format, using the following parameters for a 12-sipper chip: screening pressure—2.3 psi, upstream voltage—500, and downstream voltage—3000. These conditions cause unphosphorylated substrate and phosphorylated product peptide to resolve as separate peaks allowing direct measurement of percentage of conversion of substrate to product. The percent conversion was plotted against concentration of inhibitor to produce a sigmoidal dose response curve, from which an IC50 was calculated.

The values for the p70S6K and AKT enzyme inhibition assay for the compounds set out in the Experimental section are presented in Table 4 below.

+>15 nM
++3.0-15.0 nM
+++<3.0 nM

TABLE 4 p70S6K and AKT Enzyme Inhibition by Compound Described by Formula (I)

| Compound No. | IC$_{50}$ p70S6K (nM) | IC$_{50}$ AKT (nM) |
|---|---|---|
| 1 | +++ | ++ |
| 2 | +++ | +++ |
| 3 | ++ | ++ |
| 4 | ++ | ++ |
| 5 | +++ | ++ |
| 6 | ++ | ++ |
| 7 | ++ | ++ |
| 8 | ++ | ++ |
| 9 | ++ | ++ |
| 10 | ++ | ++ |
| 11 | ++ | +++ |
| 12 | ++ | ++ |
| 13 | ++ | + |
| 14 | ++ | ++ |
| 15 | +++ | ++ |
| 16 | +++ | +++ |
| 17 | ++ | ++ |
| 18 | +++ | + |
| 19 | ++ | + |
| 20 | +++ | ++ |
| 21 | +++ | +++ |
| 22 | +++ | +++ |
| 23 | +++ | ++ |
| 24 | +++ | ++ |
| 25 | +++ | +++ |
| 26 | ++ | ++ |
| 27 | ++ | + |
| 28 | ++ | ++ |
| 29 | +++ | ++ |
| 30 | + | + |
| 31 | ++ | ++ |
| 32 | +++ | ++ |

We claim:

1. A compound selected from:
6-{4-[1-(2-Azetidin-1-yl-ethyl)-4-(4-fluoro-3-methyl-phenyl)-1H-imidazol-2-yl]-piperidin-1-yl}-5-ethyl-pyrimidin-4-ylamine (1);

6-{4-[1-(2-Azetidin-1-yl-ethyl)-4-(4-fluoro-3-methyl-phenyl)-1H-imidazol-2-yl]-piperidin-1-yl}-5-chloro-pyrimidin-4-ylamine (2);

6-{4-[1-(2-Azetidin-1-yl-ethyl)-4-(2-isopropyl-pyridin-4-yl)-1H-imidazol-2-yl]-piperidin-1-yl}-5-isopropyl-pyrimidin-4-ylamine (3);

6-{4-[1-(2-Azetidin-1-yl-ethyl)-4-(4-fluoro-3-methyl-phenyl)-1H-imidazol-2-yl]-piperidin-1-yl}-5-isopropyl-pyrimidin-4-ylamine (4);

6-{4-[1-(2-Azetidin-1-yl-ethyl)-4-(2-trifluoromethyl-pyridin-4-yl)-1H-imidazol-2-yl]-piperidin-1-yl}-5-isopropyl-pyrimidin-4-ylamine (5);

5-Chloro-6-{4-[4-(4-fluoro-3-methyl-phenyl)-1-(1-methyl-azetidin-3-ylmethyl)-1H-imidazol-2-yl]-piperidin-1-yl}-pyrimidin-4-ylamine (6);

6-{4-[1-(2-Azetidin-1-yl-ethyl)-4-(4-fluoro-3-methyl-phenyl)-1H-imidazol-2-yl]-piperidin-1-yl}-5-(2H-pyrazol-3-yl)-pyrimidin-4-ylamine (7);

6-{4-[1-(2-Azetidin-1-yl-ethyl)-4-(4-fluoro-3-methyl-phenyl)-1H-imidazol-2-yl]-piperidin-1-yl}-5-pyridin-4-yl-pyrimidin-4-ylamine (8);

6-{4-[1-(2-Azetidin-1-yl-ethyl)-4-(4-fluoro-3-methyl-phenyl)-1H-imidazol-2-yl]-piperidin-1-yl}-5-pyridin-3-yl-pyrimidin-4-ylamine (9);

6-{4-[1-(2-Azetidin-1-yl-ethyl)-4-(2-isopropyl-pyridin-4-yl)-1H-imidazol-2-yl]-piperidin-1-yl}-5-ethoxy-pyrimidin-4-ylamine (10);

6-{4-[1-(2-Azetidin-1-yl-ethyl)-4-(2-isopropyl-pyridin-4-yl)-1H-imidazol-2-yl]-piperidin-1-yl}-5-cyclobutyl-pyrimidin-4-ylamine (11);

6-{4-[1-(2-Azetidin-1-yl-ethyl)-4-(2-isopropyl-pyridin-4-yl)-1H-imidazol-2-yl]-piperidin-1-yl}-5-isopropoxy-pyrimidin-4-ylamine (12);

6-{4-[1-(2-Azetidin-1-yl-ethyl)-4-(2-isopropyl-pyridin-4-yl)-1H-imidazol-2-yl]-piperidin-1-yl}-5-pyridin-4-yl-pyrimidin-4-ylamine (13);

6-{4-[1-(2-Azetidin-1-yl-ethyl)-4-(2-isopropyl-pyridin-4-yl)-1H-imidazol-2-yl]-piperidin-1-yl}-5-(2,2,2-trifluoro-ethoxy)-pyrimidin-4-ylamine (14);

4-Amino-6-{4-[1-(2-azetidin-1-yl-ethyl)-4-(2-isopropyl-pyridin-4-yl)-1H-imidazol-2-yl]-piperidin-1-yl}-pyrimidine-5-carbaldehyde (15);

6-{4-[1-(2-Azetidin-1-yl-ethyl)-4-(4-fluoro-3-methyl-phenyl)-1H-imidazol-2-yl]-piperidin-1-yl}-5-cyclopropyl-pyrimidin-4-ylamine (16);

6-{4-[1-(2-Azetidin-1-yl-ethyl)-4-(2-isopropyl-pyridin-4-yl)-1H-imidazol-2-yl]-piperidin-1-yl}-5-cyclopropyl-pyrimidin-4-ylamine (17);

6-{4-[1-(2-Azetidin-1-yl-ethyl)-4-(2-isopropyl-pyridin-4-yl)-1H-imidazol-2-yl]-piperidin-1-yl}-5-phenyl-pyrimidin-4-ylamine (18);

6-{4-[1-(2-Azetidin-1-yl-ethyl)-4-(2-isopropyl-pyridin-4-yl)-1H-imidazol-2-yl]-piperidin-1-yl}-5-pyridin-3-yl-pyrimidin-4-ylamine (19);

5-Ethoxy-6-{4-(3-chloro-4-fluorophenyl)-1-2-(dimethylamino-1-yl-ethyl)-1H-imidazol-2-yl]-piperidin-1-yl}-pyrimidin-4-ylamine (20);

5-Bromo-6-{4-(3-methyl-4-fluorophenyl)-1-2-(dimethylamino-1-yl-ethyl)-1H-imidazol-2-yl]-piperidin-1-yl}-pyrimidin-4-ylamine (21);

5-Chloro-6-{4-(3-methyl-4-fluorophenyl)-1-2-(dimethylamino-1-yl-ethyl)-1H-imidazol-2-yl]-piperidin-1-yl}-pyrimidin-4-ylamine (22);

5-Chloro-6-{4-(3-trifluoromethyl-4-fluorophenyl)-1-2-(dimethylamino-1-yl-ethyl)-1H-imidazol-2-yl]-piperidin-1-yl}-pyrimidin-4-ylamine (23);

5-Chloro-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (24);

5-Bromo-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (25);

5-Ethoxy-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (26);

5-Ethyl-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (27);

5-Isoproxy-6-{4-(3-trifluoromethyl-pyridin-4-yl)-1-2-(dimethylamino-1-yl-ethyl)-1H-imidazol-2-yl]-piperidin-1-yl}-pyrimidin-4-ylamine (28);

4-amino-6-{4-(3-trifluoromethyl-pyridin-4-yl)-1-2-(dimethylamino-1-yl-ethyl)-1H-imidazol-2-yl]-piperidin-1-yl}-pyrimidin-5-carbonitrile (29);

4-amino-6-{4-(3-trifluoromethyl-pyridin-4-yl)-1-2-(dimethylamino-1-yl-ethyl)-1H-imidazol-2-yl]-piperidin-1-yl}-pyrimidin-5-carboxamide (30);

6-{4-[1-(2-Ethylamino-ethyl)-4-(4-fluoro-3-trifluoromethyl-phenyl)-1H-imidazol-2-yl]-piperidin-1-yl}-5-isopropyl-pyrimidin-4-ylamine (31); and 6-{4-[1-[2-(3-Chloro-propylamino)-ethyl]-4-(4-fluoro-3-methyl-phenyl)-1H-imidazol-2-yl]-piperidin-1-yl}-5-isopropyl-pyrimidin-4-ylamine (32);

and pharmaceutically acceptable salts, solvates, or solvates of salts thereof.

2. A pharmaceutical composition comprising a compound of claim 1, or a pharmaceutically acceptable salt, or solvate thereof, as active ingredient, together with a pharmaceutically acceptable carrier.

3. A method for treating cancer selected from the group consisting of brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies, acute myelogenous leukemia, multiple myeloma, chronic myelogneous leukemia, myeloid cell leukemia, glioma and Kaposi's sarcoma, comprising administering to a subject a therapeutically effective amount of the compound of claim 1, or a pharmaceutically acceptable salt, or solvate thereof.

4. A kit consisting of separate packs of a) an effective amount of a compound of claim 1 or a pharmaceutically acceptable salt, or solvate thereof, and b) an effective amount of a further medicament active ingredient.

5. A process for the preparation of the compounds of claim 1 and pharmaceutically usable salts, tautomers and stereoisomers thereof, comprising:
reacting a compound of formula (A), wherein, LG is a leaving group:
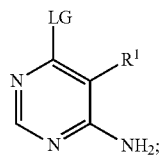
(A)
under basic conditions with compound of formula (B):
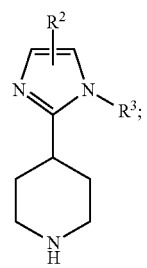
(B)
to yield the compound of the formula (I)
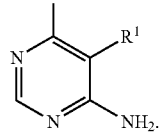
(I)
* * * * *